(12) United States Patent
Flake et al.

(10) Patent No.: US 11,471,351 B2
(45) Date of Patent: Oct. 18, 2022

(54) SYSTEM AND METHOD CONFIGURED TO PROVIDE EXTRACORPOREAL SUPPORT FOR PREMATURE FETUS

(71) Applicant: THE CHILDREN'S HOSPITAL OF PHILADELPHIA, Philadelphia, PA (US)

(72) Inventors: Alan Flake, Philadelphia, PA (US); Marcus Davey, Philadelphia, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 685 days.

(21) Appl. No.: 16/469,192

(22) PCT Filed: Dec. 13, 2017

(86) PCT No.: PCT/US2017/065950
§ 371 (c)(1),
(2) Date: Jun. 13, 2019

(87) PCT Pub. No.: WO2018/111956
PCT Pub. Date: Jun. 21, 2018

(65) Prior Publication Data
US 2019/0380900 A1 Dec. 19, 2019

Related U.S. Application Data

(60) Provisional application No. 62/434,100, filed on Dec. 14, 2016.

(51) Int. Cl.
*A61G 10/04* (2006.01)
*A61G 11/00* (2006.01)

(52) U.S. Cl.
CPC ............ *A61G 10/04* (2013.01); *A61G 11/006* (2013.01); *A61G 11/009* (2013.01)

(58) Field of Classification Search
CPC .. A61G 10/02; A61G 11/005; A61G 2200/14; A61G 10/00; A61G 10/026;
(Continued)

(56) References Cited

U.S. PATENT DOCUMENTS 2,723,660 A 11/1955 Greenberg
4,048,684 A 9/1977 Korner et al.
(Continued)

FOREIGN PATENT DOCUMENTS

CN 203663028 U 6/2014
EP 0447256 A2 9/1991
(Continued)

OTHER PUBLICATIONS

Arens et al, "NeonatOx:A Pumpless Extracorporeal Lung Support for Premature Neonates", Artificial Organs, vol. 35, No. 11, 2011, pp. 997-1001.
(Continued)

*Primary Examiner* — Christine H Matthews
(74) *Attorney, Agent, or Firm* — BakerHostetler

(57) ABSTRACT

A system configured to enclose a premature fetus within an extracorporeal environment to promote growth of the fetus and increase viability of the fetus. The system includes a chamber having an interior space configured to enclose the fetus, a first fluid circuit that delivers sterile fluid to the chamber, and a second fluid system that transfers oxygen to the fetus. The system chamber includes a stop mechanism including a clamp and an actuator, the clamp positioned in the interior space, the actuator coupled to the clamp such that movement of the actuator moves the clamp, and the actuator positioned at least partially outside the interior space.

17 Claims, 21 Drawing Sheets

(58) Field of Classification Search
CPC ...... A61G 13/101; A61G 10/04; A61G 11/00; A61G 11/006; A61G 11/009; A61G 2203/34; A61M 1/1698; A61M 1/3621; A61M 21/0094; A61M 2240/00; A61F 7/0053; A61B 17/122

See application file for complete search history.

(56) References Cited

U.S. PATENT DOCUMENTS

| | | | |
|---|---|---|---|
| 4,509,505 | A | 4/1985 | Mercey et al. |
| 4,617,912 | A | 10/1986 | Beer et al. |
| 4,796,605 | A | 1/1989 | Sasaki et al. |
| 5,063,924 | A | 11/1991 | Galvan et al. |
| 5,207,639 | A | 5/1993 | Cooper |
| 5,218,958 | A | 6/1993 | Cooper |
| 5,308,310 | A | 5/1994 | Roff et al. |
| 6,611,978 | B1 | 9/2003 | Schmidt et al. |
| 10,085,907 | B2 | 10/2018 | Flake et al. |
| 2001/0033813 | A1 | 10/2001 | Filho et al. |
| 2004/0133064 | A1 | 7/2004 | Castillon et al. |
| 2004/0193096 | A1 | 9/2004 | Cooper |
| 2005/0124850 | A1 | 6/2005 | Mackin |
| 2006/0247678 | A1* | 11/2006 | Weisenburgh, II ... A61F 2/0063 606/205 |
| 2007/0010005 | A1 | 1/2007 | Sitzmann |
| 2008/0014622 | A1 | 1/2008 | Federspiel et al. |
| 2010/0101657 | A1 | 4/2010 | Morley et al. |
| 2010/0168502 | A1 | 7/2010 | Delaporte et al. |
| 2012/0226258 | A1 | 9/2012 | Otto et al. |
| 2013/0274543 | A1 | 10/2013 | Matsubara et al. |
| 2016/0022524 | A1 | 1/2016 | Flake et al. |
| 2016/0270993 | A1 | 9/2016 | Wilden et al. |
| 2017/0128322 | A1 | 5/2017 | Fassihi et al. |

FOREIGN PATENT DOCUMENTS

| | | |
|---|---|---|
| JP | 08-294519 A | 11/1996 |
| JP | 2010-518907 A | 6/2010 |
| JP | 2013-066756 A | 4/2013 |
| JP | 2013-233194 A | 11/2013 |
| JP | 2016-064032 A | 4/2016 |
| JP | 2016-513571 A | 5/2016 |
| JP | 2016-537096 A | 12/2016 |
| RU | 2376969 C1 | 12/2009 |
| WO | 2006/125955 A1 | 11/2006 |
| WO | 2013/026148 A1 | 2/2013 |
| WO | 2013/029044 A1 | 2/2013 |
| WO | 2014/145494 | 9/2014 |
| WO | 2016/205622 A1 | 12/2016 |
| WO | 2018/171905 A1 | 9/2018 |

OTHER PUBLICATIONS

Awad et al., Pumpless Resipiratory Assistance Using a Membrane Oxygenator as an Artificial Placenta: A Preliminary Study in Newborn and Preterm Lambs, 1995, J. Invest. Surg., 8:21-30.
Behrman et al., ed., Institute of Medicine (US) Committee on Understanding Premature Birth and Assuring Healthy Outcomes; Washington DC: National Academies Press; 2007.
Boston et al., Paracorporeal lung assist device: An innovative surgical strategy for bridging to lung transplant in an infant with severe pulmonary hypertension caused by alveolar capillary dysplasia, Oct. 2013, J. Thorac. Cardiovasc. Surg., 146:e42-e43.
Callaghan et al., Studies in the Development of an Artificial Placenta, 1963, Circulation 27:686-690.
Creasy et al., Determination of Fetal, Placental and Neonatal Blood Volumes in the Sheep, Oct. 1970, Circulation Research, Res., 27:487-494.
Crossley KJ, Nicol MB, Hirst JJ, Walker DW, Thorburn GD. Suppression of arousal by progesterone in fetal sheep. Reproduction, fertility and development. 1997;9(8):767-774.
European Application 14763073, Supplementary European Search Report dated Jan. 4, 2017, 7 pages.
Faber et al., Foetal Placental Blood Flow in the Lamb, 1972, J. Pysiol., 223:375-393.
Hanif et al., Variables that affect the middle cerebral artery peak systolic velocity in fetuses with anemia and intrauterine growth restriction, Sep. 2007, Am. J. Perinatol., 24:501-505.
Huddleston et al., Lung Transplantation in Children, 2002, Ann Surg., 236:270-276.
IJsselstein et al., Long-term outcome of children treated with neonatal extracorporeal membrane oxygenation: Increasing problems with increasing age, Mar. 2014, Semin. Perinatol., 38:114-121.
International Search Report and Written Opinion issued in International Application No. PCT/US14/30277 dated Aug. 11, 2014.
Kumar et al., Post extracorporeal membrane oxygenation single photon emission computed tomography (SPECT) as a predictor of neurodevelopmental outcome, Jun. 1994, Pediatrics 93:951-955.
Kuwabara et al., Artificial Placenta: Long-Term Extrauterine Incubation of Isolated Goat Fetuses, Dec. 1989, Artificial Organs 13:527-531.
Kuwabara et al., Development of Extrauterine Fetal Incubation System Using Extracorporeal Membrane Oxygenator, 1987, Artificial Organs 11:224-227.
Martin et al., Preterm Births—United States, 2006 and 2010, MMWR Surveill. Summ., 62 (Suppl 3): 136-138, Nov. 2013.
Miura et al, "Novel Modification of an Artificial Placenta: Pumpless Arteriovenous Extracorporeal Life Support in a Premature Lamb Model", Pediatric Research, vol. 72, No. 5, Nov. 2012.
Papademetriou et al., Wavelet Cross-Correlation to Investigate Regional Variations in Cerebral Oxygenation in Infants Supported on Extracorporeal Membrane Oxygenation, 2013, Adv. Exp. Med. Biol., 765:203-209.
Reoma et al., J. Ped. Surg. (2009) 44:53-59.
Rochow et al, "Artificial Placenta—Lung Assist Devices for Term and Pre-term Newborns With Respiratory Failure", Int. J. Artif. Organs 2013; 36 (6) pp. 377-391.
Rochow et al, "Integrated Microfluidic Oxygenator Bundles for Blood Gas Exchange in Premature Infants", MEMS 2012, Paris, France, Jan. 2012, pp. 957-960.
Schoberer et al, Miniaturization: the clue to clinical application of the artificial placenta, Mar. 2014, Artificial Organs 38:208-14.
Short et al., Impairment of Cerebral Autoregulation during Extracorporeal Membrane Oxygenation in Newborn Lambs, 1993, Pediatr. Res., 33:289-294.
Stolar et al., Extracorporeal membrane oxygenation causes significant changes in intracranial pressure and carotid artery blood flow in newborn lambs, Dec. 1988, J. Pediatr. Surg., 23:1163-1168.
Unno et al., An Evaluation of the System to Control Blood flow in Maintaining Goat Fetuses on Arterio-Venous Extracorporeal membrane Oxygenation: A Novel Approach to the Development of an Artificial Placenta, Dec. 1997, Artificial Organs 21:1239-1246.
Unno et al., Development of an Artificial Placenta: Sunrival of Isolated Goat Fetuses for Three Weeks with Umbilical Arteriovenous Extracroporeal Membrane Oxygenation, Dec. 1993, Artificial Organs 17:996-1003.
Vutskits, L., Cerebral blood flow in the neonate, 2014, Pediatr. Anesth., 24:22-29.
Walker et al., Impairment of cerebral autoregulation during venovenous extracorporeal membrane oxygenation in the newborn lamb, Dec. 1996, Crit. Care Med., 24:2001-2006.
Yasufuku et al., Arterio-venous extracorporeal membrane oxygenation of fetal goat incubated in artificial amniotic fluid (Artificial placenta): Influence on lung growth and maturation, Mar. 1998, J. Pediatr. Surg., 33:442-448.
Zapol et al., Artificial Placenta: Two Days of Total Extrauterine Support of the Isolated Premature Lamb Fetus, Oct. 1969, Science 166:617-618.

\* cited by examiner

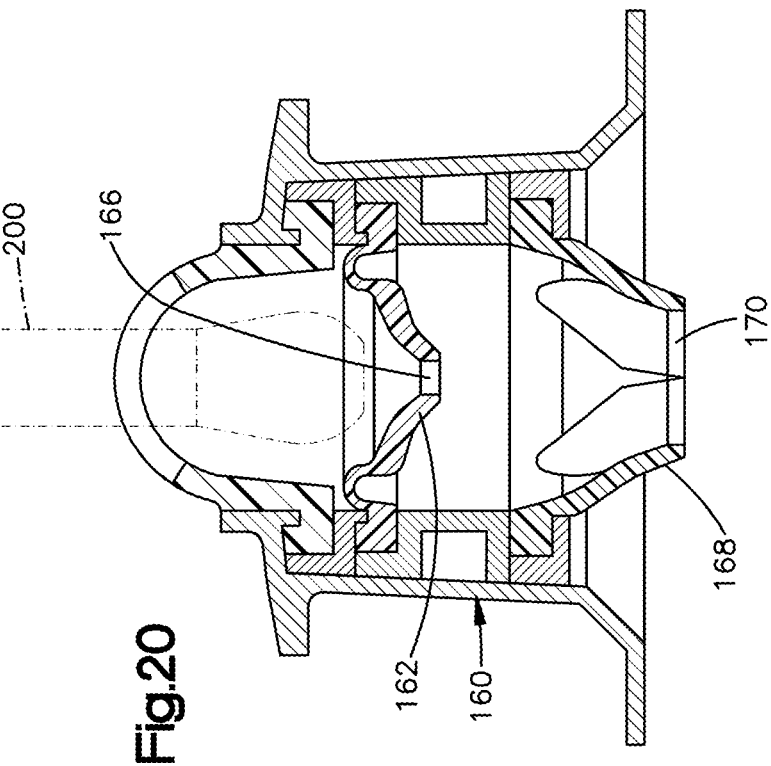
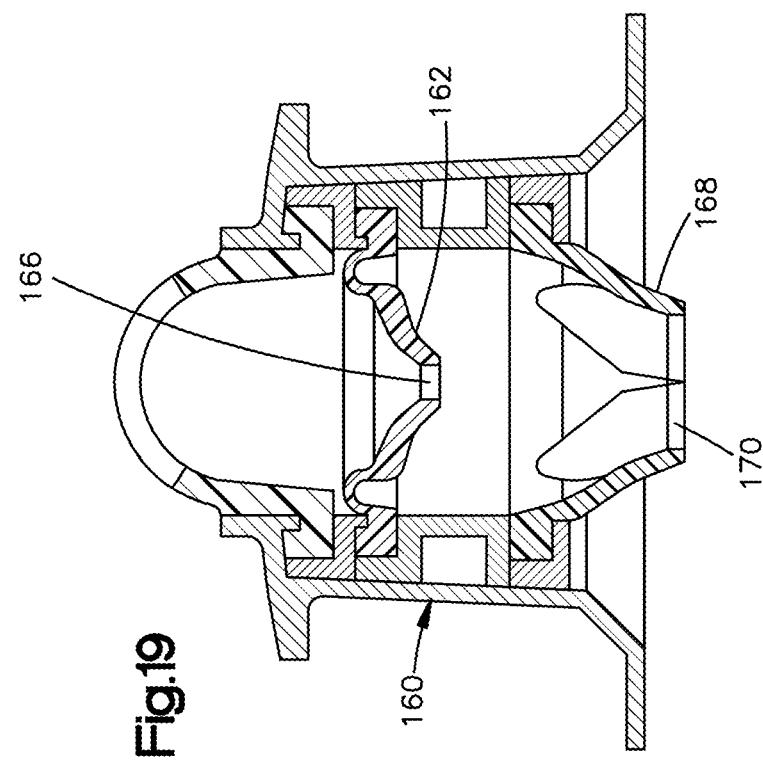

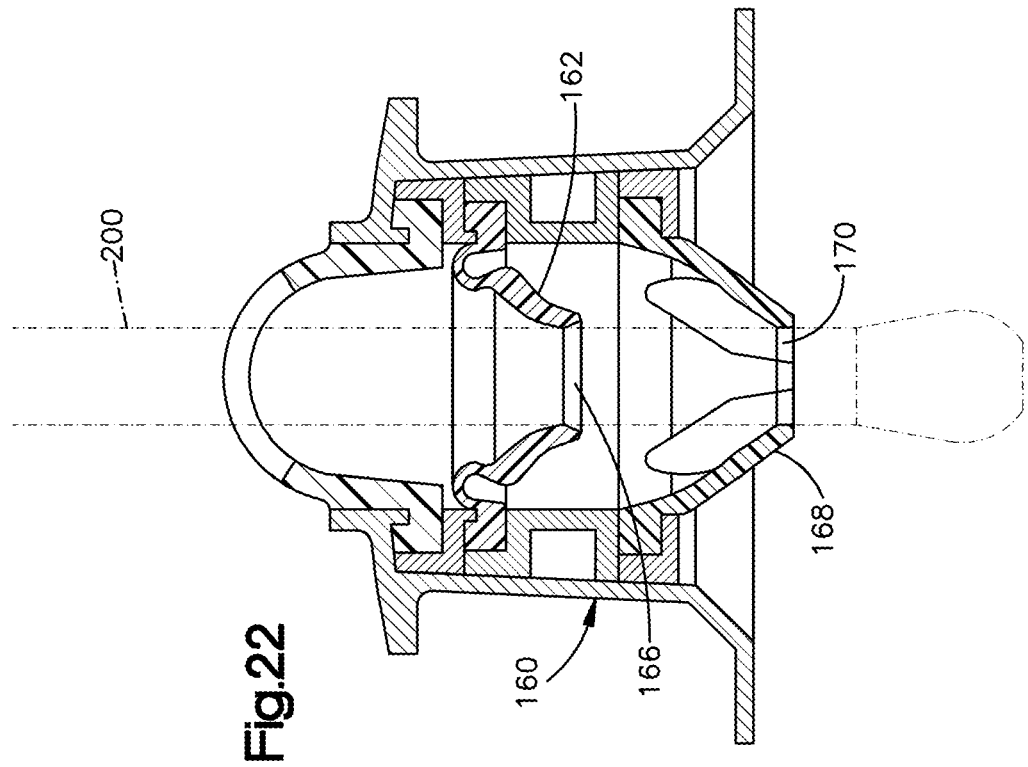
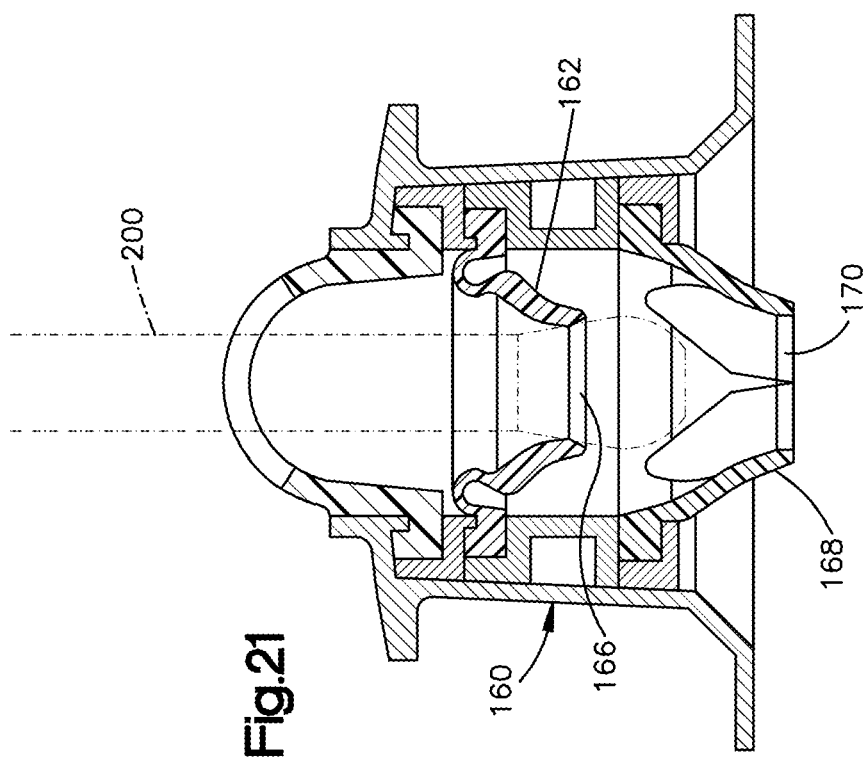

SYSTEM AND METHOD CONFIGURED TO PROVIDE EXTRACORPOREAL SUPPORT FOR PREMATURE FETUS

CROSS-REFERENCE TO RELATED APPLICATIONS

This application is the National Stage Application of International Patent Application No. PCT/US2017/065950 filed Dec. 13, 2017, which claims benefit to U.S. Provisional Application No. 62/434,100 filed Dec. 14, 2016, the disclosures of both of which are hereby incorporated by reference in their entireties herein.

TECHNICAL FIELD

The present disclosure relates generally to neonatal care. More specifically, the present disclosure describes devices, systems, and methods related to improving the viability of a premature fetus outside of the womb. According to one aspect, the present disclosure relates to improving viability of premature fetuses at a stage of development prior to 28 weeks gestation.

BACKGROUND

Extreme prematurity is the leading cause of infant morbidity and mortality in the United States, with over one third of all infant deaths and one half of cerebral palsy diagnoses attributed to prematurity. The 2010 Center for Disease Control National Vital Statistics Report notes birth rates at a gestational age of less than 28 weeks in the United States over roughly the past decade have remained stable at approximately 0.7%, or 30,000 births annually. Similarly, birth rates at gestational ages 28-32 weeks over the past decade in the United States have been stable at 1.2%, or 50,000 births annually.

Premature birth may occur due to any one of a multitude of reasons. For example, premature birth may occur spontaneously due to preterm rupture of the membranes (PROM), structural uterine features such as shortened cervix, secondary to traumatic or infectious stimuli, or due to multiple gestation. Preterm labor and delivery is also frequently encountered in the context of fetoscopy or fetal surgery, where instrumentation of the uterus often stimulates uncontrolled labor despite maximal tocolytic therapy.

Respiratory failure represents the most common and challenging problem associated with extreme prematurity, as gas exchange in critically preterm neonates is impaired by structural and functional immaturity of the lungs. Advances in neonatal intensive care have achieved improved survival and pushed the limits of viability of preterm neonates to 22 to 24 weeks gestation, which marks the transition from the canalicular to the saccular phase of lung development. Although survival has become possible, there is still a high rate of chronic lung disease and other complications of organ immaturity, particularly in fetuses born prior to 28 weeks gestation. The development of a system that could support normal fetal growth and organ maturation for even a few weeks could significantly reduce the morbidity and mortality of extreme prematurity, and improve quality of life in survivors.

The development of an "artificial placenta" has been the subject of investigation for over 50 years with little success. Previous attempts to achieve adequate oxygenation of the fetus in animal models have employed traditional extracorporeal membrane oxygenation (ECMO) with pump support, and have been limited by circulatory overload and cardiac failure in treated animals. The known systems have suffered from unacceptable complications, including: 1) progressive circulatory failure due to after-load or pre-load imbalance imposed on the fetal heart by oxygenator resistance or by circuits incorporating various pumps; and 2) contamination and fetal sepsis.

Accordingly, a system and method configured to provide extracorporeal support for a premature fetus, or fetuses (preterm or term) with inadequate respiratory gas exchange to support life, due to a spectrum of conditions/disorders, may improve viability.

SUMMARY

According to one aspect of the disclosure, a chamber configured to enclose a fetus within an interior space of the chamber is disclosed. The chamber includes a housing including a first shell and a second shell, the first shell and the second shell cooperate to at least partially define the interior space, the housing configured such that the second shell is movable with respect to the first shell from a first position to a second position, such that in the first position the chamber is in an open configuration, and in the second position the chamber is in a closed configuration. The chamber further includes a stop assembly including a clamp and an actuator, the clamp positioned in the interior space when the housing is in the closed configuration, the actuator coupled to the clamp such that movement of the actuator moves the clamp, the actuator positioned at least partially outside the interior space when the housing is in the closed configuration. When the chamber is in the open configuration the first shell and the second shell cooperatively define an opening into the interior space, the opening defines a first distance measured from a portion of the first shell to a portion of the second shell, when the chamber is in the closed configuration the opening defines a second distance measured from the portion of the first shell to the portion of the second shell, and the second distance is less than the first distance.

According to another aspect of the disclosure, a chamber configured to enclose a fetus within an interior space of the chamber is disclosed. The chamber includes an outer wall that defines an outer boundary of the interior space, an inner wall that extends from the outer wall into the interior space such that the inner wall partially defines both a first portion of the interior space and a second portion of the interior space, a clamp positioned within the second portion, the clamp movable in a direction from one of the outer wall and the inner wall toward the other of the outer wall and the inner wall, and an actuator operably coupled to the clamp such that movement of the actuator moves the clamp in the direction.

According to another aspect of the disclosure, a system configured to provide oxygen to a fetus is disclosed. The system includes a cart including a housing that defines a housing interior space, a chamber defining a chamber interior space that is sized to receive the fetus, a first fluid circuit including a container of a liquid, a pump configured to move the liquid from the source to the chamber, the pump further configured to move the liquid from the chamber to a reservoir, a second fluid circuit including an oxygenator configured to transfer oxygen to the fetus. The system defines a first configuration in which both the chamber and the oxygenator are positioned outside of the housing interior space, and the chamber is disconnected from the first fluid circuit, and the system defines a second configuration in which both the chamber and the oxygenator are positioned within the housing interior space, and the chamber is in fluid connection with the first fluid circuit.

BRIEF DESCRIPTION OF THE DRAWINGS

The foregoing summary, as well as the following detailed description of illustrative embodiments of the application, will be better understood when read in conjunction with the appended drawings. For the purposes of illustrating the present disclosure, there is shown in the drawings illustrative embodiments. It should be understood, however, that the application is not limited to the specific embodiments and methods disclosed, and reference is made to the claims for that purpose. In the drawings:

FIG. 19 is a cross-sectional view of a port of the extracorporeal support system, according to another embodiment;

FIG. 20 is a cross-sectional view of the port illustrated in FIG. 19, and a suction device, the suction device in a first position;

FIG. 21 is a cross-sectional view of the port and suction device illustrated in FIG. 20, the section device in a second position;

FIG. 22 is a cross-sectional view of the port and suction device illustrated in FIG. 20, the section device in a third position;

DETAILED DESCRIPTION OF ILLUSTRATIVE EMBODIMENTS

Figure 1:
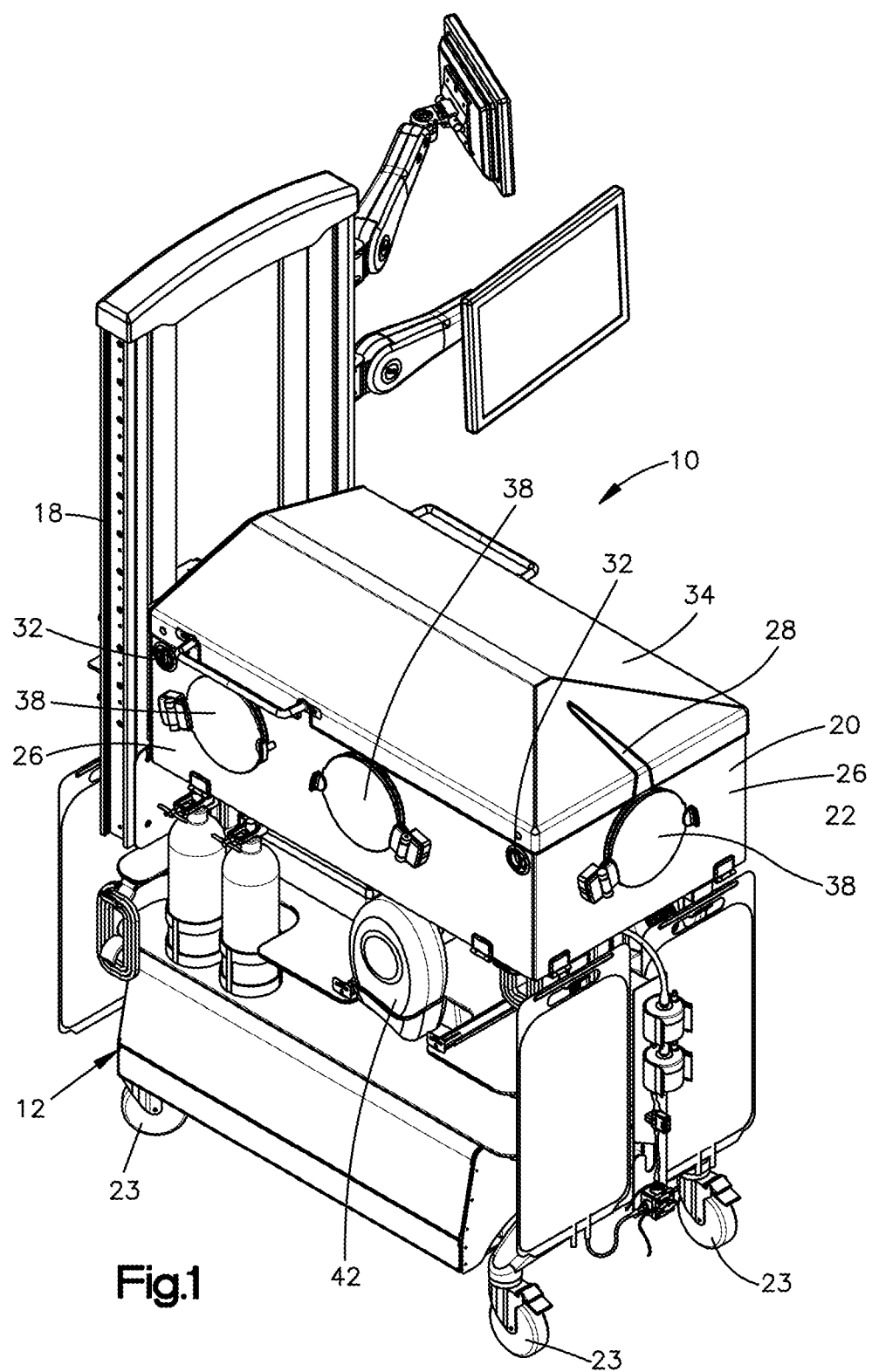
FIG. 1 is a first isometric view of an extracorporeal support system according to one embodiment, the extracorporeal support system in a first configuration.

Aspects of the disclosure will now be described in detail with reference to the drawings, wherein like reference numbers refer to like elements throughout, unless specified otherwise. Certain terminology is used in the following description for convenience only and is not limiting. The term "plurality", as used herein, means more than one. The terms "a portion" and "at least a portion" of a structure include the entirety of the structure. Certain features of the disclosure which are described herein in the context of separate embodiments may also be provided in combination in a single embodiment. Conversely, various features of the disclosure that are described in the context of a single embodiment may also be provided separately or in any subcombination.

Referring to FIGS. 1 to 4, a system 10 is configured to provide extracorporeal support to a premature fetus. According to one aspect of the disclosure the system 10 is configured to provide a system environment that is similar to an environment the premature fetus would experience in utero. Viability of a premature fetus that is removed from the uterine environment and that is, for example, between about 22 weeks to about 24 weeks gestation, may be increased by placing the premature fetus in the system environment. According to one aspect of the disclosure, the system environment is configured to: 1) limit exposure of the premature fetus to light; 2) limit exposure of the premature fetus to sound; 3) maintain the fetus submerged within a liquid environment; 4) maintain the premature fetus within a desired temperature range; or 5) any combination thereof.

The system 10 includes a cart 12 having a frame 18 and a housing 20. The frame 18 is configured to support the housing 20 such that the housing 20 is configured to at least partially contribute to providing the system environment to the premature fetus. The housing 20 includes one or more housing members 22 that at least partially define an interior space 24 that contains the system environment. As shown in the illustrated embodiment, the housing members 22 may include a plurality of side walls 26, a lid 28, and a base 30. According to one aspect of the disclosure, at least one of the plurality of side walls 26, the lid 28, or both are moveable.

Figure 2:
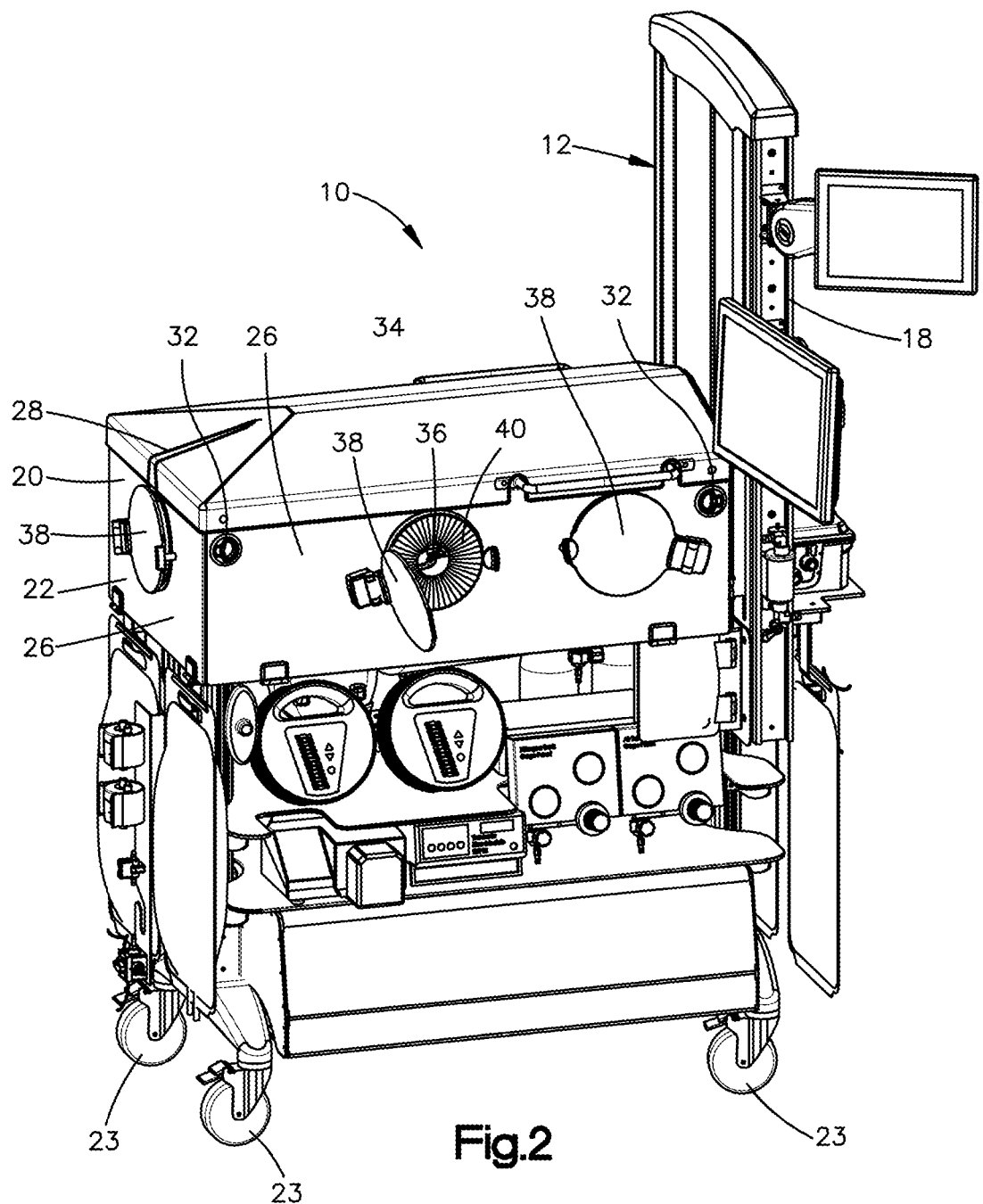
FIG. 2 is a second isometric view of the extracorporeal support system illustrated in FIG. 1, the extracorporeal support system in the first configuration.
Figure 3:
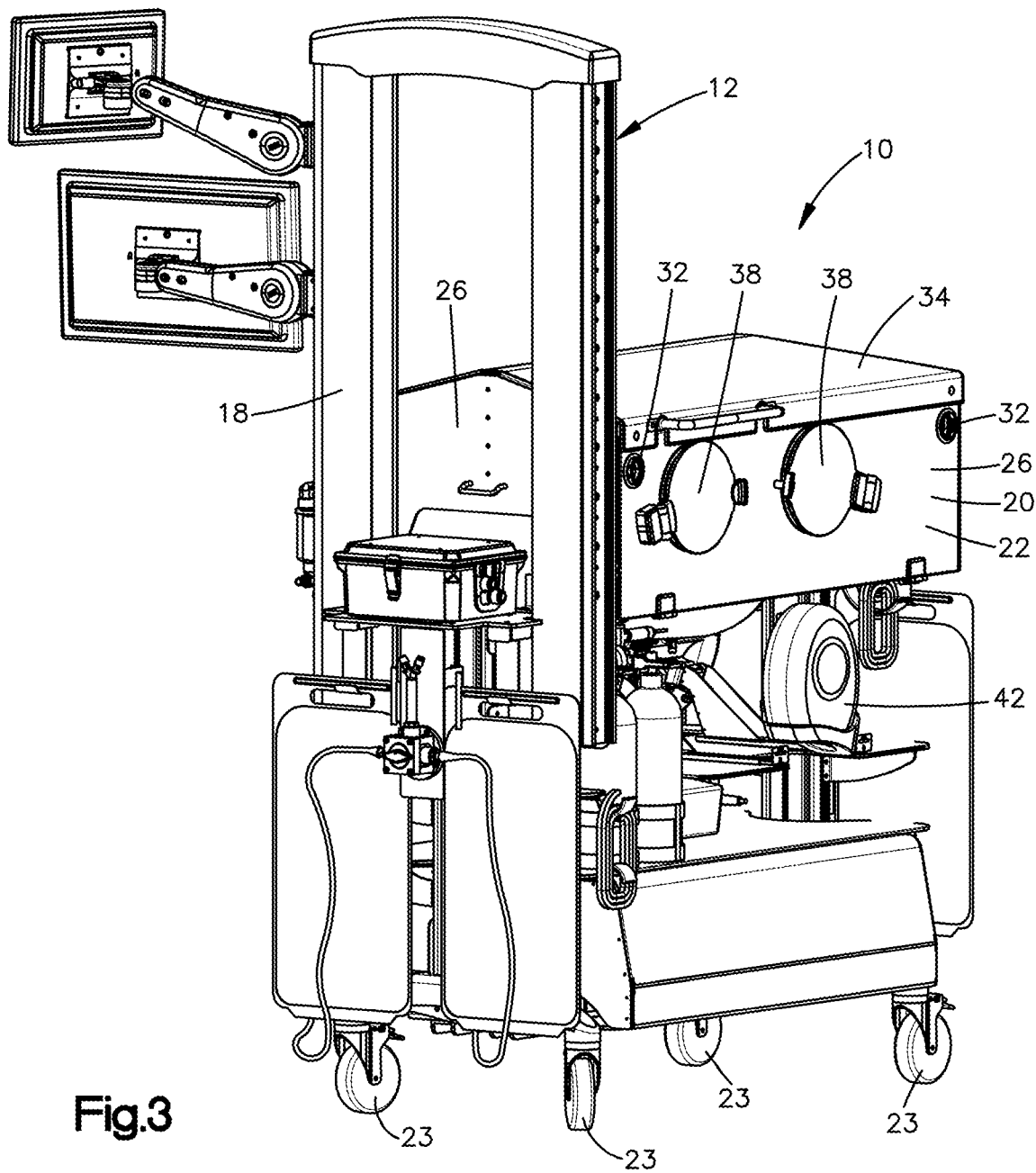
FIG. 3 is a third isometric view of a portion of the extracorporeal support system illustrated in FIG. 1, the extracorporeal support system in the first configuration.
Figure 4:
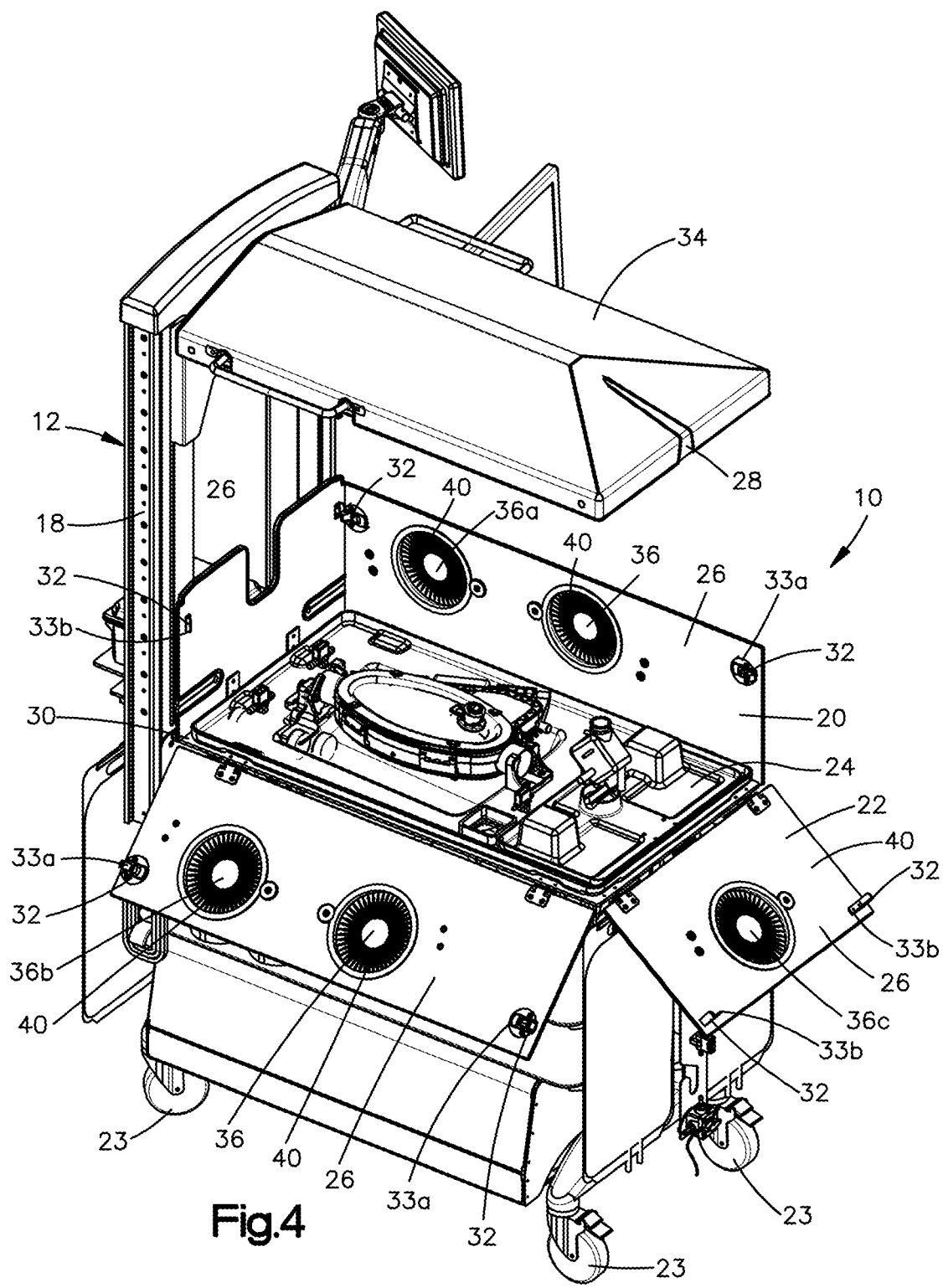
FIG. 4 is an isometric view of the extracorporeal support system illustrated in FIG. 1, the extracorporeal support system in a second configuration.

The housing 20 defines a first configuration, an example of which is shown in FIGS. 1, 2, and 3, in which the plurality of side walls 26 and the lid 28 are arranged to cooperatively define the interior space 24. In the first configuration the housing 20 is configured to maintain the system environment and restrict access to the interior space 24. The housing 20 defines a second configuration, an example of which is shown in FIG. 4, in which the plurality of side walls 26 and the lid 28 are arranged to provide increased access to the interior space 24.

As shown in the illustrated embodiment, the housing 20 may include four side walls 26. One or more of the side walls 26, for example all four, three, two, or one of the side walls 26, may be pivotally coupled to the frame 18. As shown in FIGS. 1, 2, and 3, in the first configuration the side walls 26, the lid 28, and the base 30 cooperate to define the interior space 24. As shown in FIG. 4, in the second configuration one or more of the side walls 26 are pivoted away from others of the side walls 26 such that the interior space 24 is accessible from an exterior of the system 10. The housing 20 may include a locking mechanism 32 configured to: 1) secure the side walls 26 in the first configuration when the locking mechanism 32 is engaged, and 2) allow the side walls 26 to pivot when the locking mechanism 32 is disengaged.

As shown in the illustrated embodiment, the locking mechanism 32 may include corresponding members located on adjacent ones of the plurality of side walls 26. For example the locking mechanism may include a latch 33a located on one of the side walls 26 and a projection 33b configured to be captured by the latch 33a thereby securing the adjacent ones of the plurality of side walls 26 to one another.

As shown in the illustrated embodiment, the lid 28 may be translatable with respect to the side walls 26. The system 10 may be configured such that the lid 28 is translatable along a vertical direction, which is substantially perpendicular to a surface upon which the system 10 is positioned, for example a floor, such as a hospital floor. According to one aspect of the disclosure, in the first configuration the lid 28 is in close proximity, for example touching, one or more of the side walls 26, and in the second configuration an entirety of the lid 28 is spaced from the floor a distance of at least about six feet, for example about seventy-one inches. The system 10 may be further configured such that when the entirety of the lid 28 is spaced from the floor by a distance of at least about six feet, an entirety of the system 10 is positioned less than seventy-nine inches from the floor.

The amount of clearance under the lid 28 is configured to allow a maximum amount of space for a person, such as a doctor or nurse, to access the system 10 without interference from the lid 28, and the maximum height of the system 10 is configured to allow the system 10 to pass through a standard size hospital doorway. According to another aspect of the disclosure, in the second configuration an entirety of the lid 28 may be spaced from the floor a distance less than six feet, a portion of the system 10 may be spaced from the floor by a distance greater than seventy-nine inches, or both.

According to another embodiment, the side walls 26 and the lid 28 may be an integral or monolithic piece. According to another embodiment, the side walls 26 and the lid 28, whether separate or monolithic, may be translatable, pivotable, or both relative to the frame 18.

The lid 28 may be transparent such that a person outside of the system 10 can view the interior space 24 of the system 10 when the housing 20 is in the first configuration. The housing 20 may further include a removable, opaque cover 34 that prevents light from a source outside of the interior space 24 from reaching the interior space 24 through the transparent lid 28. The system 10 may be configured to limit the amount of light that reaches the interior space 24 when the system 10 is in the first configuration to about 1.2 lux or below. According to one embodiment, the opaque cover 34 may be secured to the housing 20 magnetically. Alternatively, the lid 28 may be opaque. The system 10 may be configured to provide an indirect view of the interior space 24, for example the system 10 may include a camera positioned inside the interior space 24 that transmits an image to a screen outside the interior space 24.

The housing 20 may be configured such that the lid 28 remains in the second configuration without a person exerting an external force on the lid 28. For example, the housing 20 may include a constant force spring assembly that provides a retention force that holds the lid 28 at its current distance from the floor until an external force, in addition to the force of gravity, is applied to the lid 28.

The housing 20 may be configured to provide access to the interior space 24 when the housing 20 is in the first configuration. As shown in the illustrated embodiment, the housing 20 includes one or more access ports 36 that are each configured to provide a passageway for a person's hand from an exterior of the system 10 to the interior space 24. The access ports 36 may each include a respective cover 38 configured to block the access port 36. Each of the respective covers 38 may be configured to be moved relative to the access port 36 thereby providing access to the passageway. The access port 36 may include a flexible iris 40 configured to provide a seal around an arm of the person using the access port 36 to access the interior space 24.

According to one aspect of the disclosure, the access ports 36 are positioned such that a portion of the access port 36 is between about 3 feet and about 4 feet from the floor. For example, a center of the access port 36 may be positioned about forty-three inches from the floor. The access ports 36 may be positioned such that different ones of the access ports 36 provide access to the interior space 24 along different directions. As shown in the illustrated embodiment, the system 10 may include: a first one of the access ports 36a configured to provide access to the interior space 24 along a first direction; a second one of the access ports 36b configured to provide access to the interior space 24 along a second direction that is opposite the first direction; a third one of the access ports 36c configured to provide access to the interior space 24 along a third direction that is perpendicular to both the first direction and the second direction, or any combination thereof.

The system 10, according to one embodiment, may include a heater 42 configured to maintain the interior space 24 within a desired temperature range. For example, the heater 42 may be configured to maintain a temperature within the interior space 24 between about twenty-eight degrees Celsius and about thirty-eight degrees Celsius, preferably between about thirty degrees Celsius and about thirty-four degrees Celsius, for example about thirty-two degrees Celsius. The system 10 according to one embodiment, may include a sound dampening system configured to dampen the amplitude of sound that reaches the interior space 24 of the system 10 when the housing is in the first configuration to below about 20 decibels. According to one embodiment, the sound dampening can be achieved by attaching sound dampening material to one or more of the side walls 26.

The system 10 may be mobile such that system is configured to be moveable from one location to another while still providing appropriate levels of oxygen delivery to the interior space 24, for example to a fetus in the interior space 24. According to one aspect of the disclosure, the system 10 may include a plurality of wheels 23 enabling the system 10 to be moved, for example from an operating room to a neonatal intensive care unit. As shown in the illustrated embodiment, the wheels 23 are coupled to the cart 12.

Figure 5:
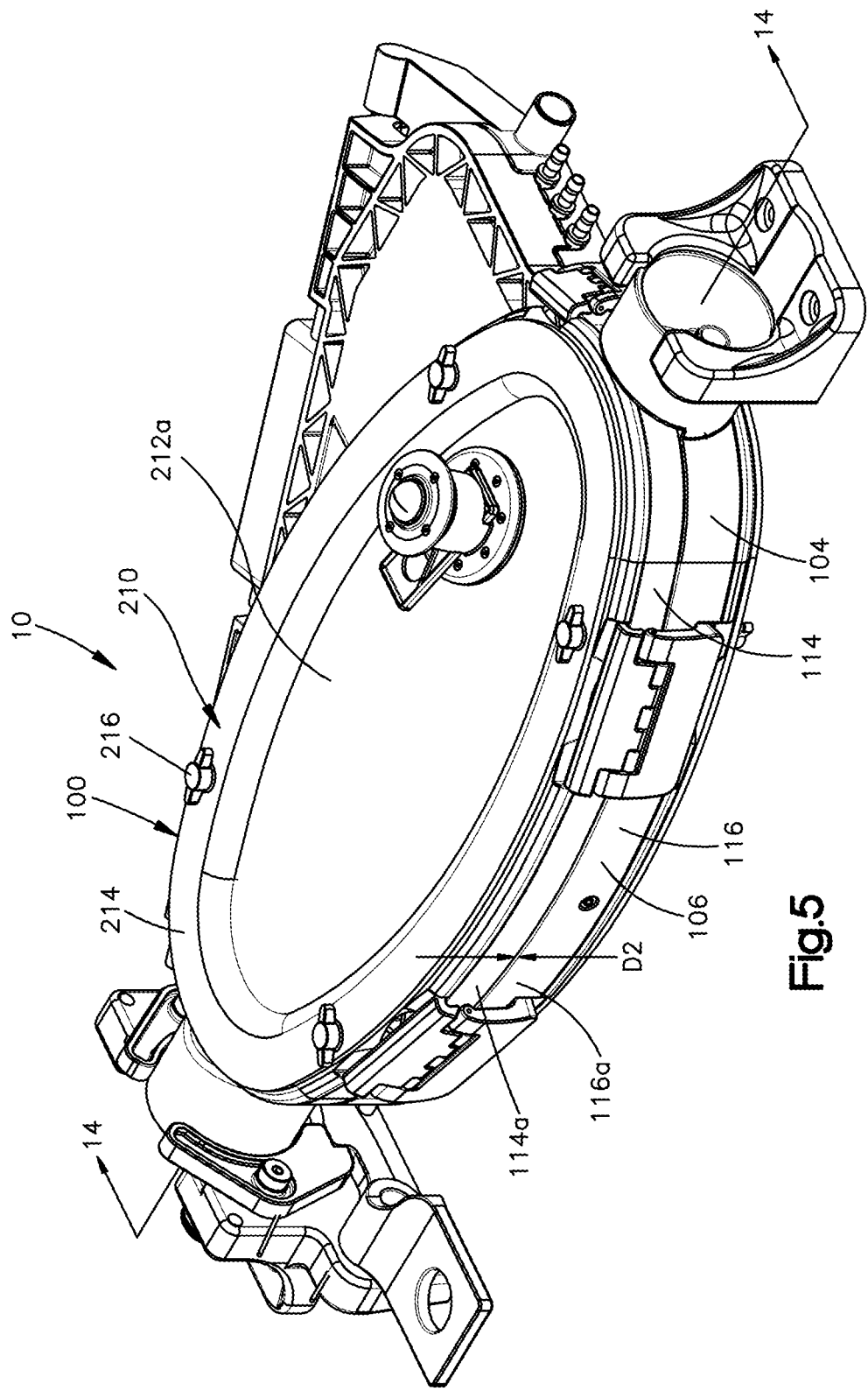
FIG. 5 is an isometric view of a fetal chamber of the extracorporeal support system according to one embodiment, the fetal chamber in a first configuration.
Figure 6:
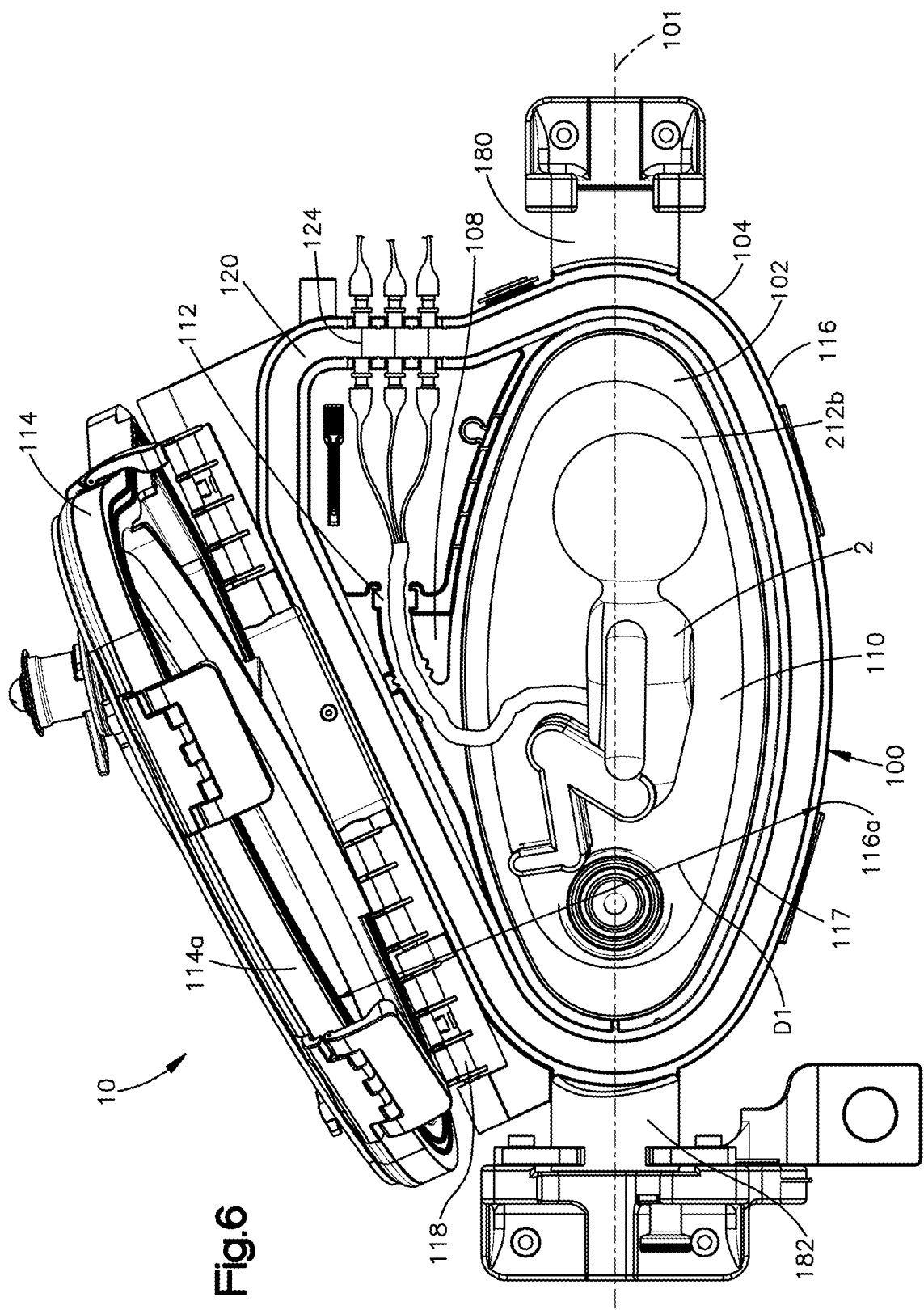
FIG. 6 is a top plan view of the fetal chamber illustrated in FIG. 5, the fetal chamber in a second configuration.

Referring to FIGS. 5 and 6, the system 10 includes a chamber 100 configured to receive and enclose a fetus 2, for example a premature, human fetus, within an extra uterine, enclosed environment. According to one aspect of the disclosure, the cart 12 is configured to enclose the chamber 100 within the interior space 24. The chamber 100 defines a chamber interior space 102 that contains the extra uterine, enclosed environment. The chamber 100 defines a first configuration, also referred to herein as an open configuration, as shown in FIG. 6. In the open configuration the chamber interior space 102 is accessible such that the chamber interior space 102 is configured to receive the fetus 2. The chamber 100 defines a second configuration, also referred to herein as a closed configuration, as shown in FIG. 5. In the closed configuration the chamber interior space 102 is sealed off from the environment surrounding the chamber 100.

The chamber 100 includes a chamber housing 104 that defines the chamber interior space 102. According to one aspect of the disclosure, the chamber housing 104 may include an outer chamber wall 106 that defines an outer boundary of the chamber interior space 102. As shown in the illustrated embodiment, the outer chamber wall 106 defines an outer perimeter of the chamber 100 when the chamber 100 is in the closed configuration. The chamber housing 104 may further include an inner chamber wall 108 that at least partially separates a first portion 110 of the chamber interior space 102 from a second portion 112 of the chamber interior space 102.

According to one aspect of the disclosure, when the chamber 100 is in the open configuration a first shell 114 of the housing and a second shell 116 of the housing cooperatively define an opening 117 into the interior chamber space 102, the opening 117 defines a first distance D1 measured from a portion 114a of the first shell 114 to a portion 116a of the second shell 116. When the chamber 100 is in the closed configuration the opening 117 defines a second distance D2 measured from the portion 114a of the first shell 114 to the portion 116a of the second shell 116. The second distance D2 is less than the first distance D1. As shown in the illustrated embodiment, the second distance D2 may be zero such that the portion 114a and the portion 116a abut. According to another embodiment D2 may be greater than zero.

The system 10 may be configured such that the chamber 100 is rotatable about an axis 101, relative to the cart 12. The axis 101 may be a longitudinal axis that the chamber 100 is elongate along. As shown in the illustrated embodiment, the axis 101 may pass through a first end 180 of the chamber 100 and a second end 182 of the chamber 100. According to one embodiment, the chamber 100 is rotatable about the axis 101 through a full revolution of 360 degrees. According to another embodiment, the chamber 100 is rotatable about the axis 101 through less than a full revolution of 360 degrees.

For example, the chamber 100 may be rotatable about the axis 101 about 180 degrees clockwise from the position shown in FIG. 6, and rotatable about 180 degrees counterclockwise from the position shown in FIG. 6. The system 10 being configured such that the chamber 100 is rotatable about the axis 101 relative to the cart 12 allows the position of the fetus 2 to be adjusted while maintaining the chamber 100 in the closed configuration. Adjustment of the position of the fetus 2 may reduce or eliminate dependent edema, fetal asymmetry, pressure sores, or other undesired conditions.

The chamber 100 defines a length measured along the axis 101, a width measured along a lateral direction perpendicular to the axis 101, and a height measured along a vertical direction that is perpendicular to both the axis 101 and the lateral direction. According to one embodiment, the chamber 100 defines a maximum length measured along the axis 101, a maximum width measured along a line that is perpendicular to the axis 101 and that intersects the first shell 114 in two separate locations, and a maximum height measured along a line that is perpendicular to both the axis 101 and the lateral direction and that intersects both the first shell 114 and the second shell 116 when the chamber 100 is in the closed configuration. As shown in the illustrated embodiment, the chamber 100 may be configured such that the maximum length is greater than the maximum width, and the maximum width is greater than the maximum height.

The chamber 100 may include a volume adjustment assembly 210 configured to change, for example increase, decrease, or both, a volume defined by the interior space 102 when the chamber 100 is in the closed configuration. The chamber 100 may include at least one flexible wall 212. As shown in the illustrated embodiment, the first shell 114 may include a first flexible wall 212a and the second shell 116 may include a second flexible wall 212b. The volume adjustment assembly 210 may include a member 214 configured to be coupled to the chamber housing 104 such that the member 214 deforms at least one of the flexible walls 212 thereby reducing the volume of the interior space 102 compared to when the member 214 is not coupled to the chamber housing 104.

Figure 7:
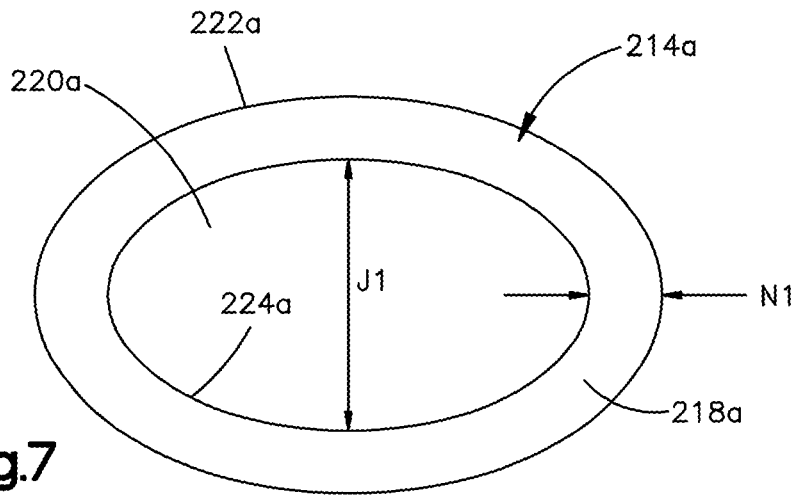
FIG. 7 is a top plan view of a first member of a volume adjustment assembly.
Figure 8:
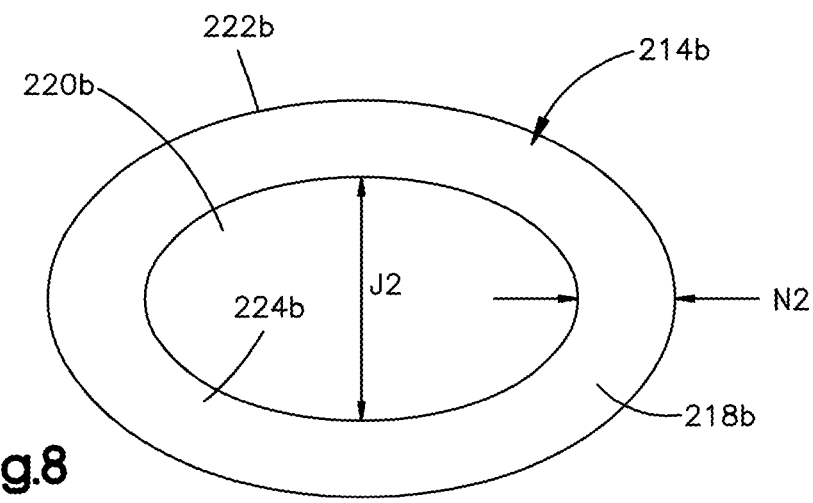
FIG. 8 is a top plan view of a second member of a volume adjustment assembly.
Figure 9:
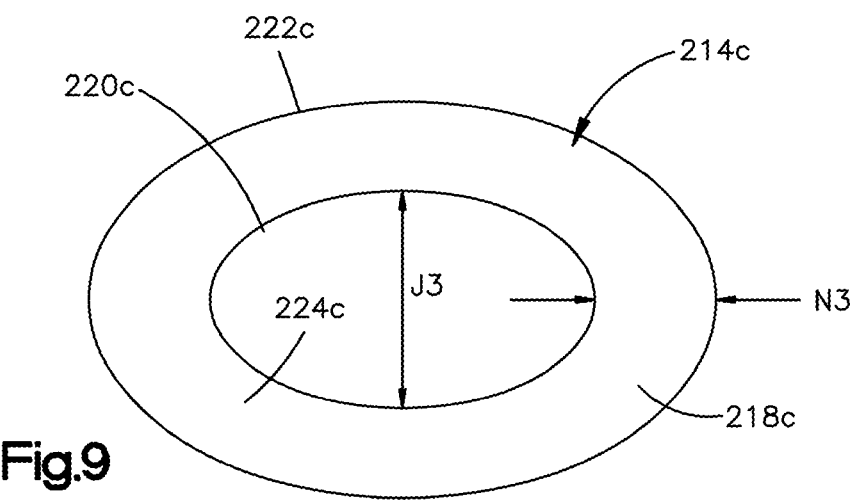
FIG. 9 is a top plan view of a third member of a volume adjustment assembly.

Referring to FIGS. 7 to 9, according to one aspect of the disclosure, the volume adjustment assembly 210 includes a plurality of members 214. Each of the plurality of member 214 may be configured to limit the maximum value of the volume of the interior space 102 when the chamber 100 is in the closed configuration. For example, the plurality of members 214 may each define an outer ring 218 and an opening 220 defined by the outer ring 218 such that the opening 220 is at least partially enclosed by the outer ring 218 within a plane P1. The plurality of members 214 may include a first member 214a, a second member 214b, a third member 214c.

As shown in the illustrated embodiment, the opening 220a of the first member 214a defines a first cross-sectional area J1 measured within the plane P1. The opening 220b of the second member 214b defines a second cross-sectional area J2 measured within the plane P1. The opening 220c of the third member 214c defines a third cross-sectional area J3 measured within the plane P1. According to one aspect of the disclosure, the plurality of members 214 are configured such that the first cross-area J1 is greater than the second cross-sectional area J2, and the second cross-sectional area J2 is greater than the third cross-sectional area J3. The plurality of members 214 may further be configured such that the third member 214c restricts the maximum volume of the interior space 102 more than when the third member 214c is coupled to the chamber housing 104 than when the second member 214b is coupled to the chamber housing 104. The plurality of members 214 may further be configured such that the second member 214b restricts the maximum volume of the interior space 102 when the second member 214b is coupled to the chamber housing 104 more than when the first member 214a is coupled to the chamber housing 104.

According to one aspect of the disclosure, the maximum volume of the interior space 102 without any of the plurality of members 214 attached may be about 3.6 Liters. The plurality of members 2144 may be configured such that the third member 214c restricts the maximum volume of the interior space 102 to a volume sufficient to accommodate a fetus of about 22 weeks estimated gestational age, the second member 214b restricts the maximum volume of the interior space 102 to a volume sufficient to accommodate a fetus of about 24 weeks estimated gestational age, the first member 214a restricts the maximum volume of the interior space 102 to a volume sufficient to accommodate a fetus of about 26 weeks estimated gestational age, or any combination thereof.

According to one aspect of the disclosure the plurality of members 2144 may be configured such that the third member 214c restricts the maximum volume of the interior space 102 to a volume of about 15 liters, the second member 214b restricts the maximum volume of the interior space 102 to a volume of about 2 liters, the first member 214a restricts the maximum volume of the interior space 102 to a volume of about 2.5 liters, or any combination thereof.

According to one aspect of the disclosure, the ring 218a of the first member 214a, the second member 214b, and the third member 214c each define an equal outer perimeter 222a, 222b, and 222c, and different inner perimeters 224a, 224b, and 224c, respectively. Thus the first member 214a, the second member 214b, and the third member 214c may each define different thickness N1, N2, and N3, respectively, measured in the plane P1.

Thus the plurality of members 214 may be configured to be sequentially coupled to the chamber housing 104 to incrementally increase the maximum volume of the interior space 102 to correspond to growth of the fetus 2. For example, the chamber 100 may be configured for use such that when the fetus 2 is first placed inside the interior space 102, the third member 214c is coupled to the chamber housing 104 to restrict the maximum volume of the interior space 102 and limit movement, for example rotation, of the fetus 2 within the interior space 2. As the fetus 2 develops and grows, more volume within the interior space 102 may be needed. Accordingly, the third member 214c may be decoupled from the chamber housing 104 and the second member 214b may be coupled to the chamber housing 104, all while the chamber 100 remains in the closed configuration. With the second member 214b coupled to the chamber housing 104, the maximum volume of the interior space 102 is greater than it was within the third member 214c coupled to the chamber housing 104.

As the fetus 2 develops and grows further, more volume within the interior space 102 may be needed. Accordingly, the second member 214b may be decoupled from the chamber housing 104 and the first member 214a may be coupled to the chamber housing 104, all while the chamber 100 remains in the closed configuration. With the first member 214a coupled to the chamber housing 104, the maximum volume of the interior space 102 is greater than it was within the second member 214b coupled to the chamber housing 104. Although described as including third members, the plurality of members 214 may include more than three members.

Referring again to FIGS. 5 and 6, the volume adjustment assembly 210 may be adjustable such that the volume of the interior space 102 is selectable between a range of volumes. As shown in the illustrated embodiment, the volume adjustment assembly 210 may include an adjustment mechanism 216 such as an internally threaded nut. The adjustment mechanism 216 may include a first position in which the volume adjustment assembly 210 defines a minimum volume of the interior space 102. For example, the adjustment mechanism 216 may be tightened all the way down, for example the threaded nut may be bottomed out, such that the member 214 deforms the flexible wall 212 towards the interior space 102 a maximum distance.

The adjustment mechanism 216 may include a second position in which the volume adjustment assembly 210 defines a maximum volume of the interior space 102. For example, the adjustment mechanism 216 may be loosened all the way, for example the threaded nut, the member 212 or both may be removed from the chamber housing 104, such that the member 214 deforms the flexible wall 212 towards the interior space 102 a minimum distance, for example not at all. The inclusion of a volume adjustment assembly 210 allows adjustment of the volume of the interior space 102 while the chamber 100 is in the closed configuration. A chamber 100 capable of varying the volume of the interior space 102 while the chamber 100 is in the closed configuration enables the chamber 100 to adapt to the fetus 2 as the fetus 2 develops, for example the volume of the interior space 102 can be increased to accommodate the increasing size of the fetus 2 as the fetus matures, without the need to remove the fetus 2 from the interior space 102.

Figure 10:
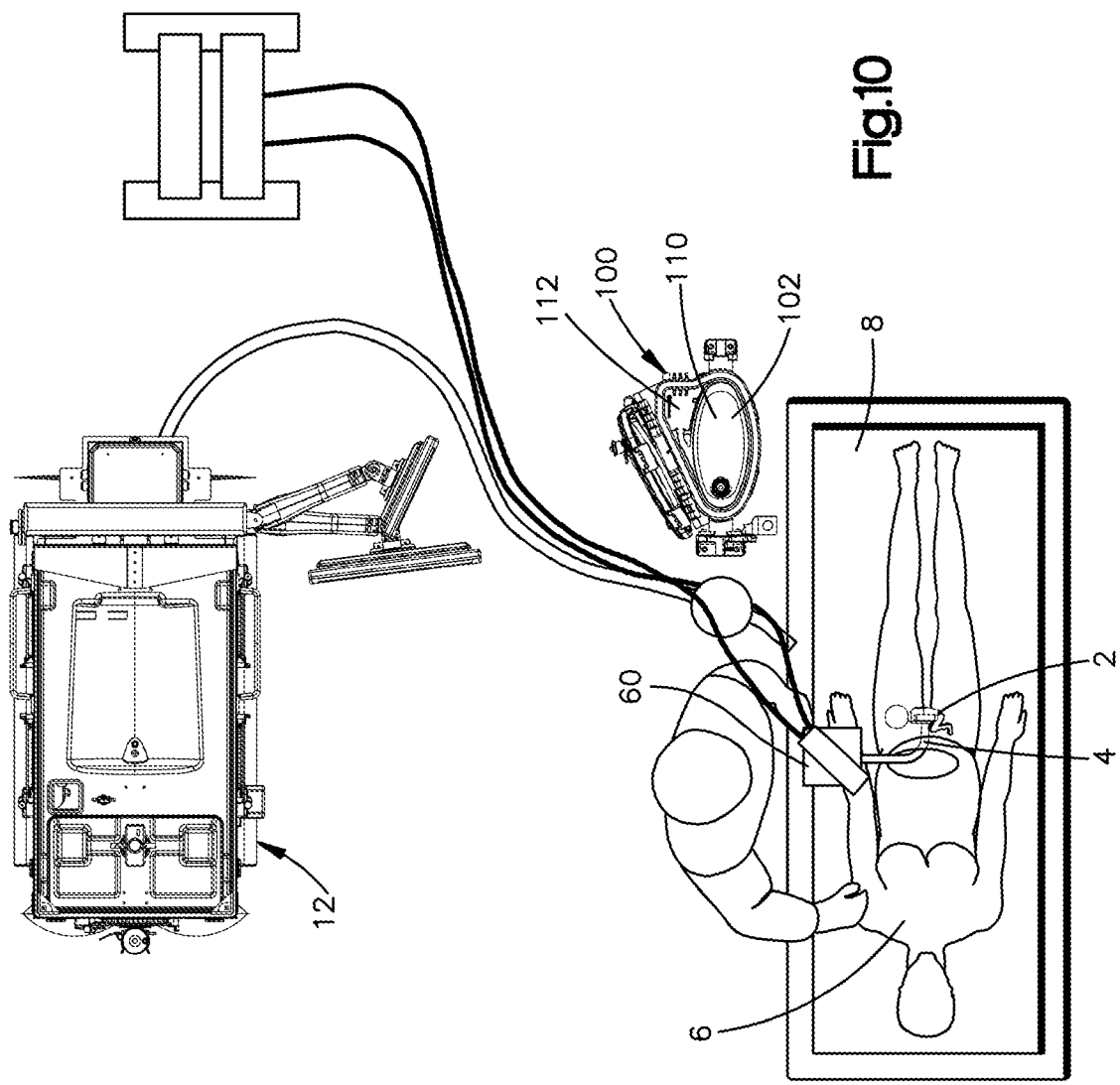
FIG. 10 is a schematic view of the extracorporeal support system illustrated in FIG. 1, in use in an operating room.

Referring to FIG. 10, a method of moving a premature fetus 2 from the uterus of a patient 6 to an ex utero environment is provided. The method includes the step of accessing the umbilical cord 4 of the fetus 2. According to one aspect of the disclosure, the accessing step includes making an opening in the uterus of the patient 6 while maintaining uteroplacental perfusion and flow through the umbilical cord. Once the uterus is open and umbilical cord exposed, the method includes the steps of cannulating the umbilical cord vessels (2 arteries and one vein), connecting the cannulas to an oxygenator 60, and then clamping the umbilical cord and severing the umbilical cord 4. The severing step may include the step of separating the fetus from the placenta by clamping and dividing the umbilical cord on the placental side of the cord relative to the cannulas. The connecting step includes the step of attaching the fetus 2 to the oxygenator 60 such that deoxygenated blood is delivered from the fetus 2 to the oxygenator 60, and oxygenated blood is delivered from the oxygenator 60 to the fetus 2. According to one aspect of the disclosure, the method may include, before the attaching step, the step of priming the oxygenator 60, for example with blood.

The step of cannulating the fetus 2 may include the steps of: attaching a first cannula to a vein of the umbilical cord 4, attaching a second cannula to a first artery of the umbilical cord 4, attaching a third cannula to a second artery of the umbilical cord 4, or any combination thereof. The method may further include the step of connecting one or more of the first, second and third cannulae to an oxygenation circuit, which includes the oxygenator 60.

The method further includes the steps of removing the fetus 2 from the uterus of the patient 6 and positioning the fetus 2 within the chamber 100. The method may include the steps of removing the chamber 100 from the cart 12 and positioning the chamber 100 in close proximity to the patient 6, for example on an operating room table 8 upon which the patient 6 is positioned. The system being configured such that the chamber 100 is removable from the cart 12, for example to a location closer to the patient 6 than the cart 12 would be able to go, may reduce the amount of time the fetus 2 is exposed to an ex utero environment during the method, and reduce the potential for contamination, thereby reducing the risk to the fetus 2.

The method further includes, after the cannulating step, the step of positioning the fetus 2 within the chamber interior space 102, and after the positioning step, the step of transitioning the chamber 100 from the open configuration to the closed configuration. The method may further include the step of attaching the chamber 100, with the fetus 2 positioned in the chamber interior space 102, to the cart 12. The method may further include, after the transitioning step, the step of pumping a fluid, for example a sterile fluid, into the chamber interior space 102. The method may include, prior to the pumping step, the step of heating the fluid to a desired temperature, for example a temperature above the ambient room temperature. According to one embodiment, the desired temperature may be in the range of about twenty-eight degrees Celsius to about thirty-eight degrees Celsius, more specifically the desired temperature may be in the range of about thirty degrees Celsius to about thirty-four degrees Celsius. As shown in the illustrated embodiment, the first portion 110 may be configured to receive the fetus 2 and the second portion 112 may be configured to receive at least a portion of the umbilical cord 4 of the fetus 2.

Figure 11:
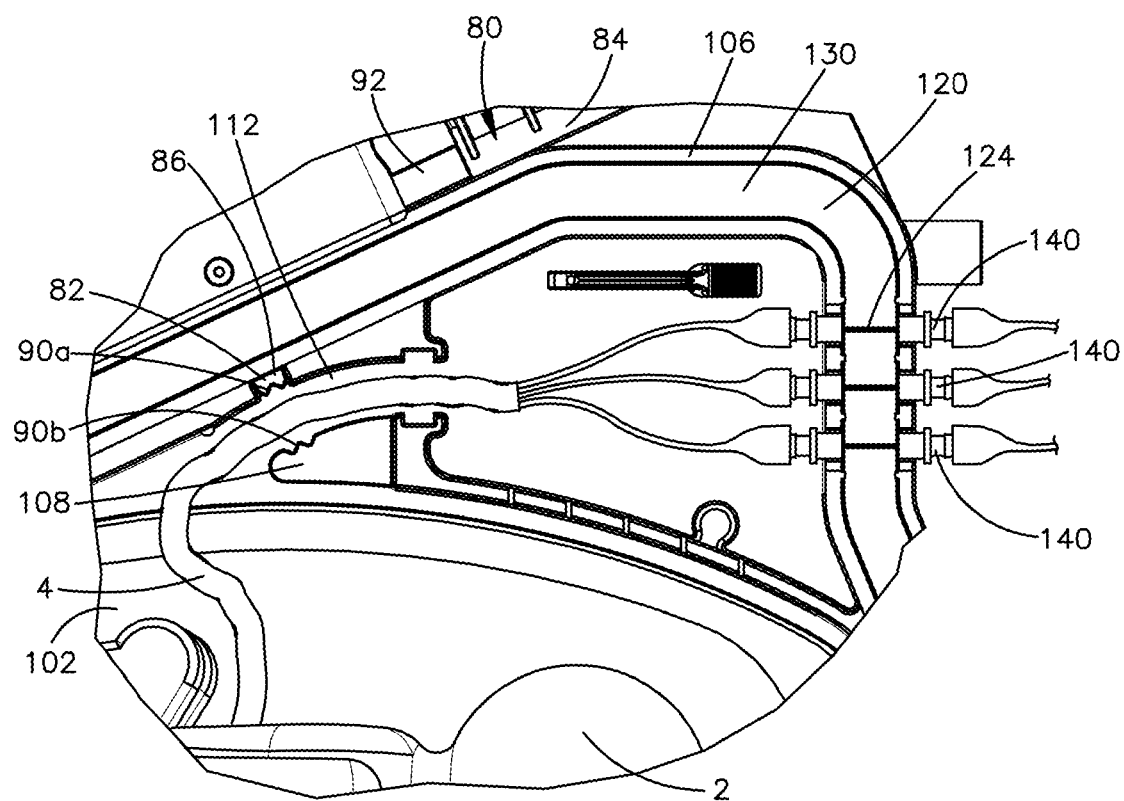
FIG. 11 is an isometric view of a portion of the fetal chamber illustrated in FIG. 5, the portion including an emergency clamp assembly, the emergency clamp assembly is a first configuration.
Figure 12:
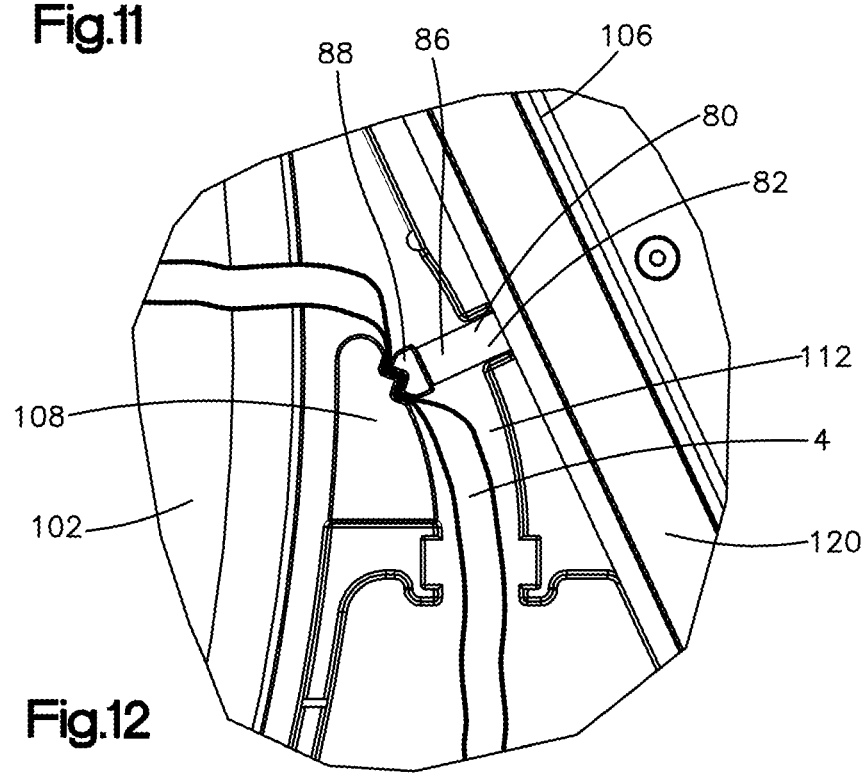
FIG. 12 is an isometric view of a portion of the fetal chamber illustrated in FIG. 5, the portion including the emergency clamp assembly in a second configuration.

Referring to FIGS. 11 and 12, the system 10 may include a stop assembly 80 configured to clamp the umbilical cord 4 of the fetus 2. According to one aspect of the disclosure, the chamber interior space 102, for example the second portion 112, may be configured to receive a portion of the umbilical cord 4. As shown in the illustrated embodiment the chamber 100 can be configured to receive the umbilical cord 4 between a portion of the outer chamber wall 106 and a portion of the inner chamber wall 108.

As shown in FIGS. 11 and 12, he stop assembly 80 may include a clamp 82 and an actuator 84, the actuator 84 operatively coupled to the clamp 82 such that input, for example by a person operating the system 10, to the actuator 84 transitions the clamp 82 from a first position, illustrated in FIG. 11, also referred to herein as an open position, to a second position, illustrated in FIG. 12, also referred to herein as a closed position. As shown in FIG. 11, in the open configuration the second portion 112 is unobstructed by the clamp 82 such that when the umbilical cord 4 is positioned within the second portion 112 the umbilical cord 4 is unaltered by the clamp 82. As shown in FIG. 12, in the closed configuration the second portion 112 is at least partially obstructed, for example fully obstructed, by the clamp 82 such that when the umbilical cord 4 is positioned within the second portion 112 the umbilical cord 4 is altered, for example clamped such that blood flow through the umbilical cord 4, is prevented.

Prior to placement of the fetus 2 within the chamber interior space 102, at least one cannula 140 may be connected to the fetus 2. As shown a plurality of cannulae 140, for example three cannulae 140, may be connected to the umbilical cord 4 of the fetus 2 such that each of the cannulae 140 is in fluid connection with the circulatory system of the fetus 2. After the umbilical cord 4 of the fetus 2 is cannulated, and the fetus is placed into the chamber interior space 102, one or more of the cannulae 140 may become detached at any time during treatment of the infant 2 such that the one or more of the cannulae 140 are no longer in fluid connection with the circulatory system of the fetus 2, referred to herein as a decannulation event. A decannulation event may pose a risk of serious blood loss for the fetus 2 and thereby a risk to the viability of the fetus 2.

The system 10 may include a decannulation detection assembly configured to detect a decannulation event. According to one embodiment, the system may include a camera configured to detect blood within the interior space 102, which may be an indication of a decannulation event. The camera may be configured to operate and detect blood in the interior space 102 in low light conditions.

The stop assembly 80 is configured to clamp the umbilical cord 4 of the fetus 2 thereby preventing further blood loss after a decannulation event. As shown in the illustrated embodiment, the clamp 82 may include a piston 86 positioned in proximity to, for example within, one of the outer chamber wall 106 and the inner chamber wall 108 when the clamp 82 is in the first position. In the second position the piston 86 extends out from the one of the outer chamber wall 106 and the inner chamber wall 108 toward, for example to, the other of the outer chamber wall 106 and the inner chamber wall 108. According to one aspect of the disclosure, the clamp 82, for example a tip 88 of the piston 86, a portion of the chamber housing 104 that is opposite the clamp 82, or both include an uneven surface 90a and 90b that faces toward the other of the clamp 82 or the portion of the chamber housing 104. The uneven surface 90a and 90b may be configured to provide better clamping of the umbilical cord 4 than an even surface would provide.

The actuator 84 may include a handle 92 operably coupled to the clamp 82 such that actuation, for example rotation, of the handle 92 transitions the clamp 82, for example the piston 86 from one of the first position and the second position to the other of the first position and the second position. The actuator 84 is positioned such that the actuator 84 can be operated to transition the clamp 82 from the first position to the second position while the chamber 100 is in the closed configuration. Thus a method of providing care for the fetus 2, for example the method of moving the fetus 2 from the uterus of a patient 6 to an ex utero environment, may include the step of providing an input to a stop assembly, thereby clamping the umbilical cord 4 of the fetus 2.

Figure 13:
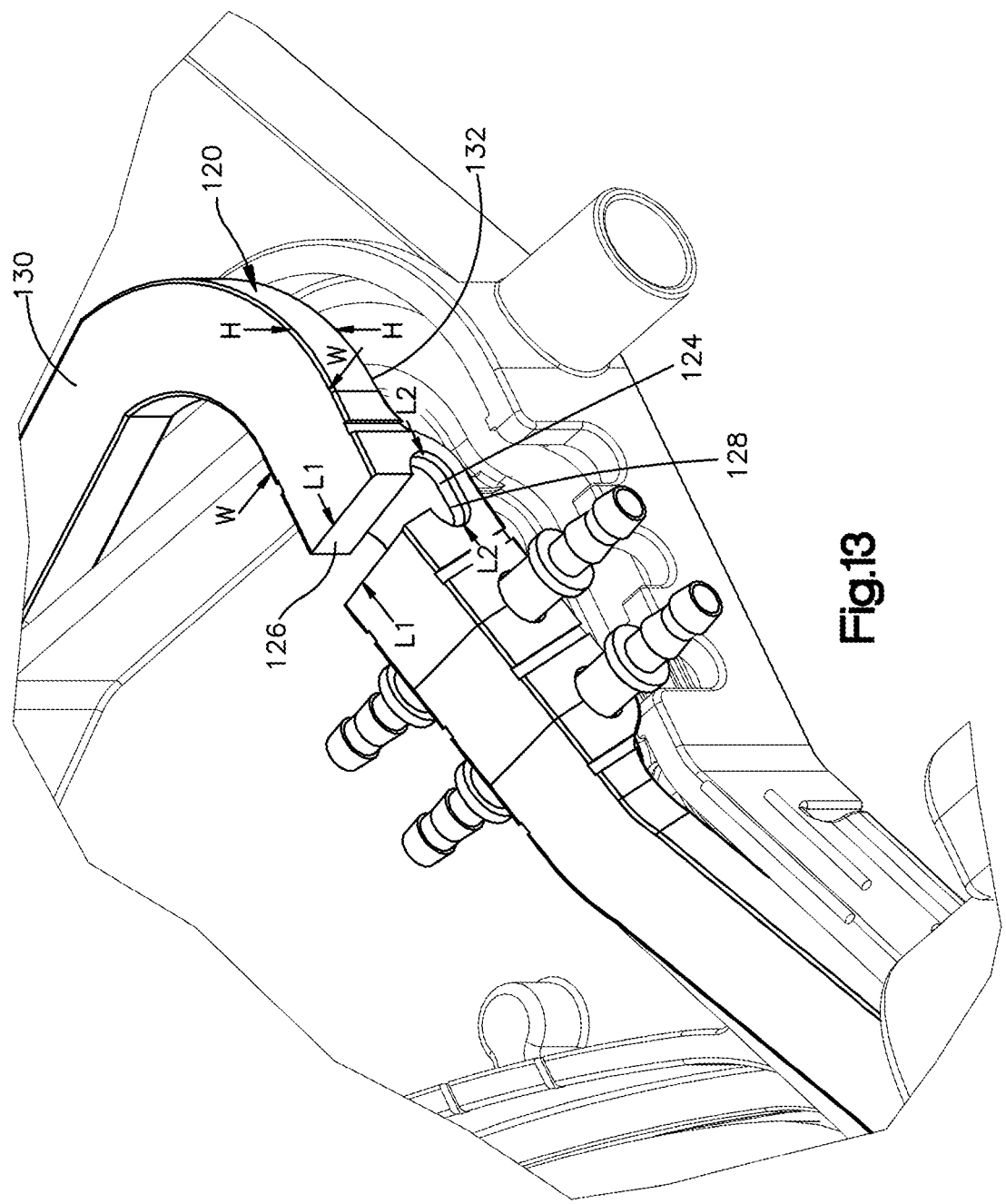
FIG. 13 is an isometric view of a seal of the fetal chamber according to one aspect of the disclosure.

Referring to FIGS. 6, 11, and 13, the chamber housing 104, for example the outer chamber wall 106, includes a first shell 114 and a second shell 116 that are movable relative to one another thereby allowing transition of the chamber 100 from the open configuration to the closed configuration. As shown in the illustrated embodiment, at least one of the first shell 114 and the second shell 116 is rotatable with respect to the other of the first shell 114 and the second shell 116, about at least one hinge 118.

According to one aspect of the disclosure, the chamber includes a seal 120 that includes a resilient material, such that the seal 120 is configured to be compressed between the first shell 114 and the second shell 116 when the chamber 100 is in the closed configuration, and the seal 120 is further configured to expand from the compressed state to an uncompressed state when the chamber 100 is in the open configuration. As shown in the illustrated embodiment, the chamber housing 104, for example the first shell 114, the second shell 116, or both, defines a recess 122 configured to at least partially receive the seal 120. In the closed configuration the seal 120 provides a liquid tight barrier between the chamber interior space 102 and the environment surrounding the chamber 100.

According to one aspect of the disclosure, the seal 120 defines a height H that is measured between the first shell 114 and the second shell 116 when the chamber 100 is in the closed configuration, and the seal further defines a width W that is perpendicular to the height H. As shown in the illustrated embodiment, the width W may be measured between the chamber interior space 102 and the environment surrounding the chamber 100.

The seal 120 defines at least one slot 124 configured to receive at least one of the cannulae 140 that are connected to the fetus 2. The slot 124 may include a first portion 126 that defines a first length L1 that is perpendicular to both the height H and the width W. The slot may include a second portion 128 that defines a second length L2 that is perpendicular to both the height H and the width W. Both the first length L1 and the second length L2 may be measured from one side wall of the seal 120 to an opposing side wall of the seal 120 that faces the one side wall. According to one aspect of the disclosure the first length L1 is less than the second length L2.

As shown in the illustrated embodiment, the first portion 126 of the slot 124 may extend from a first outer surface 130 of the seal 120 toward a second outer surface 132 of the seal 120 that is opposite the first outer surface 130 of the seal 120. The first outer surface 130 and the second outer surface 132 may each be surfaces that the height H is normal to. The seal 120 may terminate prior to reaching the second outer surface 132 of the seal 120. As shown the first portion 126 is positioned between the first outer surface 130 and the second portion 128 with respect to the direction the height H is measured along.

The slot 124 may be configured to receive the cannula 140 when the chamber 100 is in the open configuration. The cannula 140 may be moved through the first portion 126 of the slot 124 and then positioned within the second portion 128 of the slot 124. When the cannula 140 is positioned within the second portion 128, transitioning the chamber 100 into the closed configuration causes both the first portion 126 to form a liquid tight barrier and the second portion 128 to form a liquid tight barrier around the cannula 140. As shown in the illustrated embodiment, the seal 120 may define three of the slots 124 arranged such that the slots 124 extend through the seal 120 substantially perpendicular to one another. The seal 120 may include other numbers of the slots 124, for example less than three or more than three, and other arrangements of the slots 124, for example non-parallel to one another. As shown in the illustrated embodiment, the slot 124 may face the second portion 112 of the chamber interior space 102.

Figure 14:
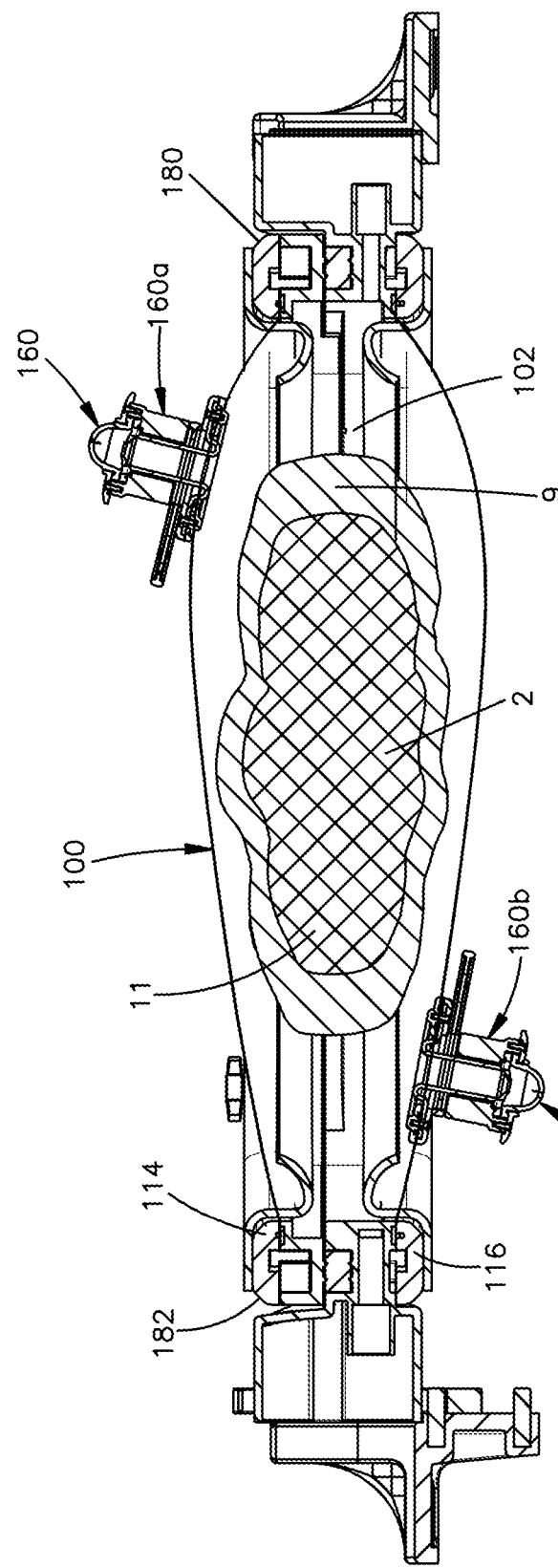
FIG. 14 is a cross-sectional view of the fetal chamber illustrated in FIG. 5 along line 14-14, the fetal chamber including a port.

Referring to FIG. 14, the chamber 100 may include a port 160 configured to provide a passageway from the environment surrounding the chamber 100 to the chamber interior space 102 when the chamber 100 is in the closed configuration. As shown in the illustrated embodiment the chamber 100 may include a plurality of ports 160 including a first port 160a and a second port 160b. The first port 160a and the second port 160b may be positioned opposite one another. For example the first port 160a may be supported by the first shell 114 and the second port 160b may be supported by the second shell 116. The first port 160a may be positioned closer to the first end 180 of the chamber 100 than the second port 160b is to the first end 180, and the second port 160b may be positioned closer to the second end 182 of the chamber 100 than the first port 160a is to the second end 182. As shown in the illustrated embodiment, the first port 160a and the second port 160b may be positioned such that when the fetus 2 is in the chamber 100 and the chamber 100 is in the closed configuration, the first port 160a is positioned proximate the head 7 of the fetus 2 and the second port 160b is positioned proximate the feet 9 of the fetus 2. The chamber 100 including the first port 160a proximate the fetus' head and the second port 160b proximate the fetus' feet provides selectable access to the chamber interior space 102 to remove debris from the chamber interior space 102 that is positioned either by the head 7 or feet 9 of the fetus 2.

Figure 15:
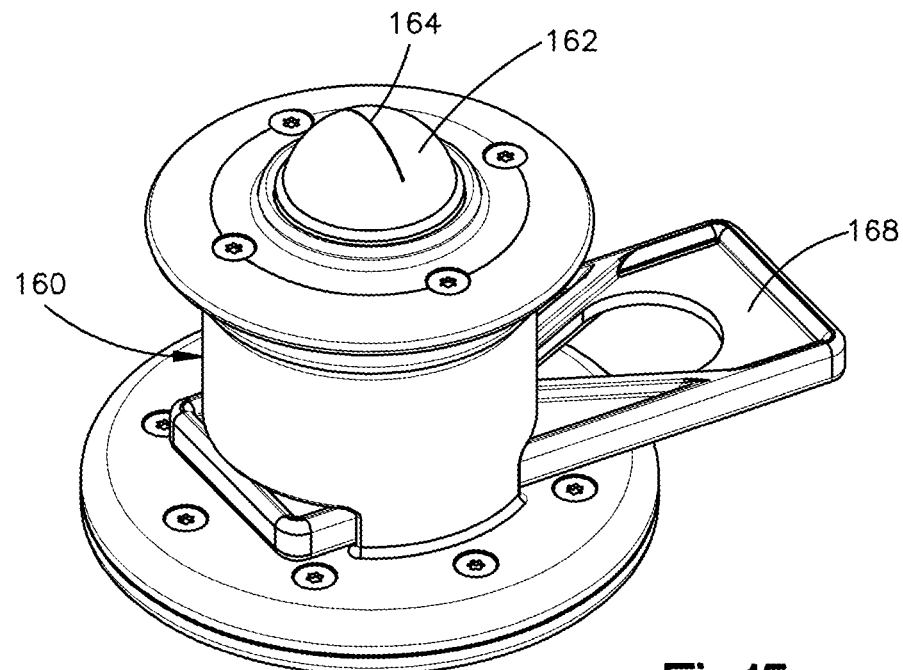
FIG. 15 is an isometric view of the port illustrated in FIG. 14, according to one embodiment, in a first configuration.
Figure 16:
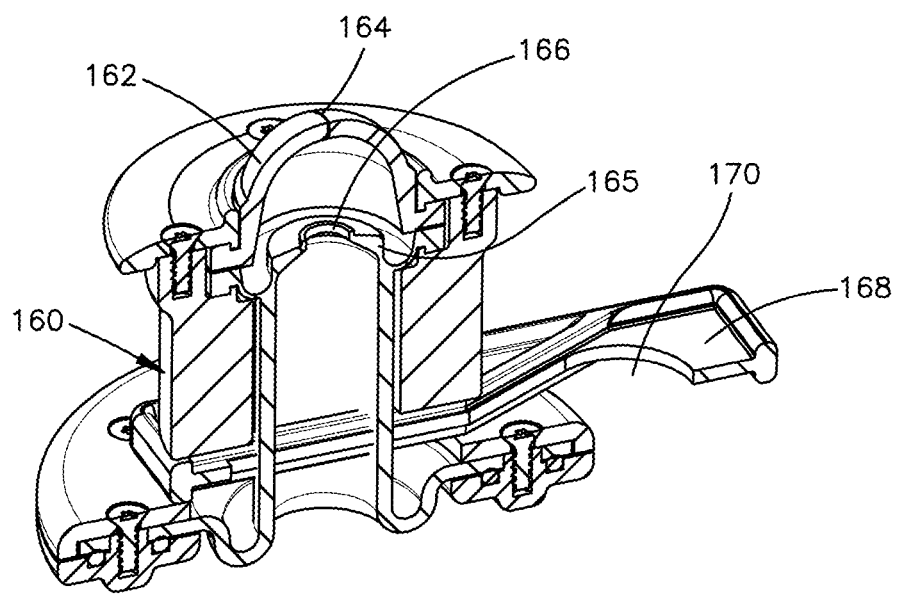
FIG. 16 is a cross-sectional view of the port illustrated in FIG. 15 in the first configuration.
Figure 17:
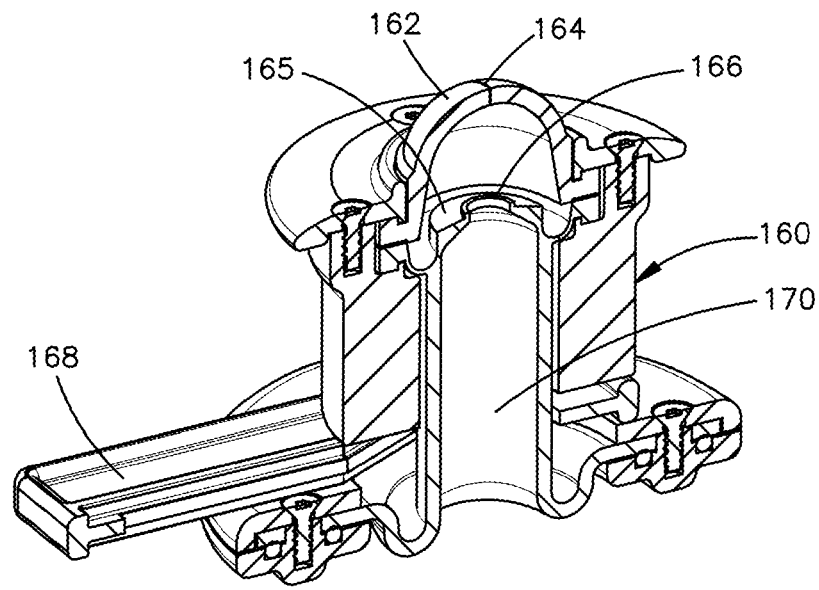
FIG. 17 is a cross-sectional view of the port illustrated in FIG. 15 in a second configuration.
Figure 18:
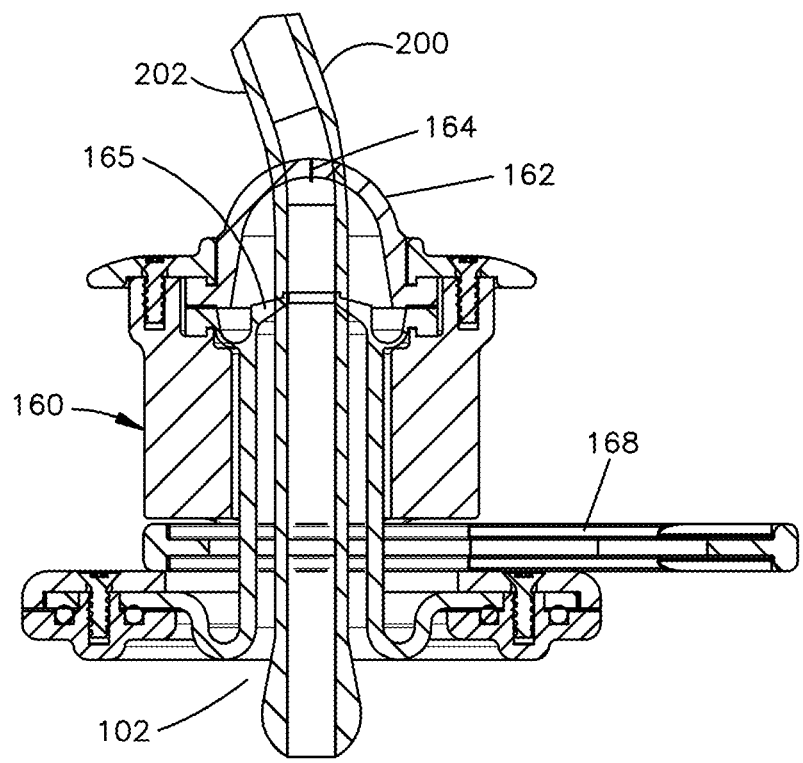
FIG. 18 is a cross-sectional view of the port illustrated in FIG. 15 in the second configuration, and a suction device.
Figure 23:
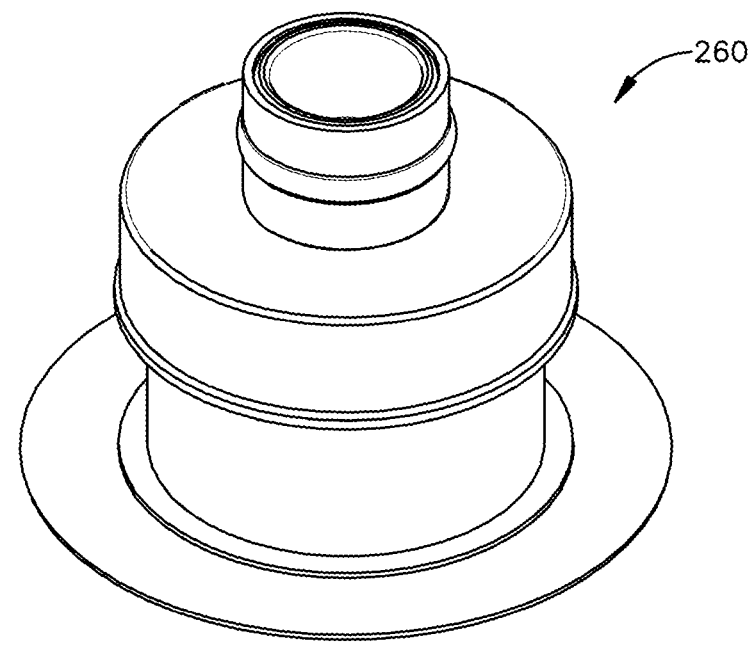
FIG. 23 is an isometric view of a port of the extra corporeal support system, according to another embodiment.
Figure 24:
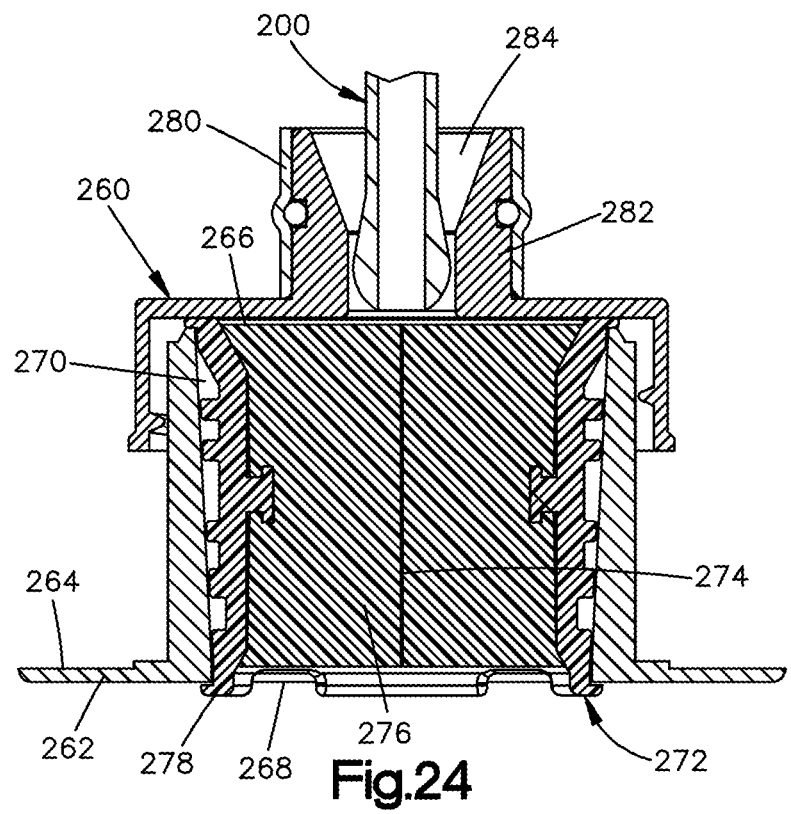
FIG. 24 is a side cross-sectional view of the port illustrated in FIG. 23 and a suction device in a first position relative to the port.
Figure 25:
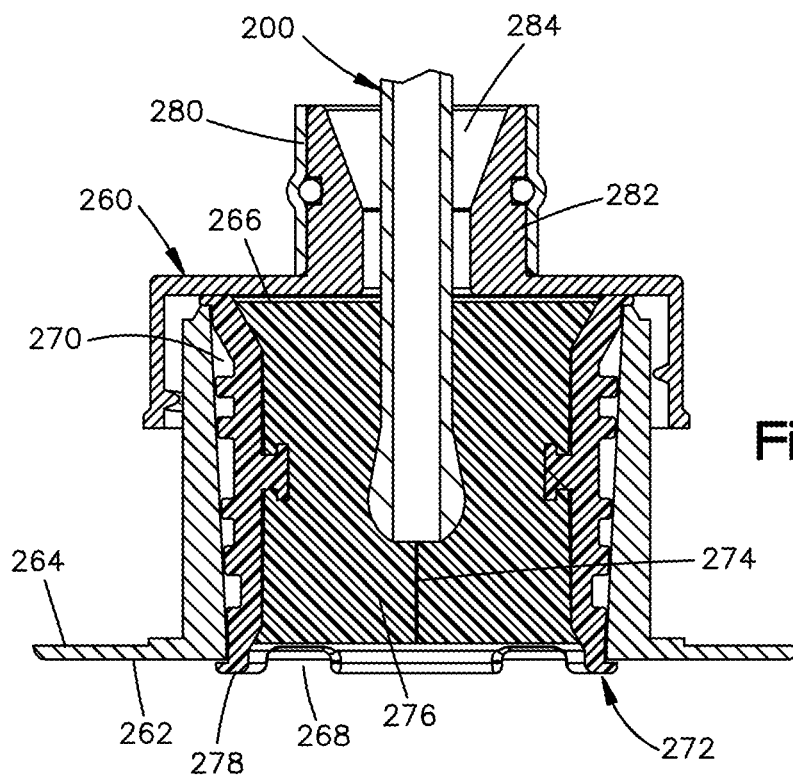
FIG. 25 is a side cross-sectional view of the port and the suction device illustrated in FIG. 25, the suction device in a second position relative to the port.
Figure 26:
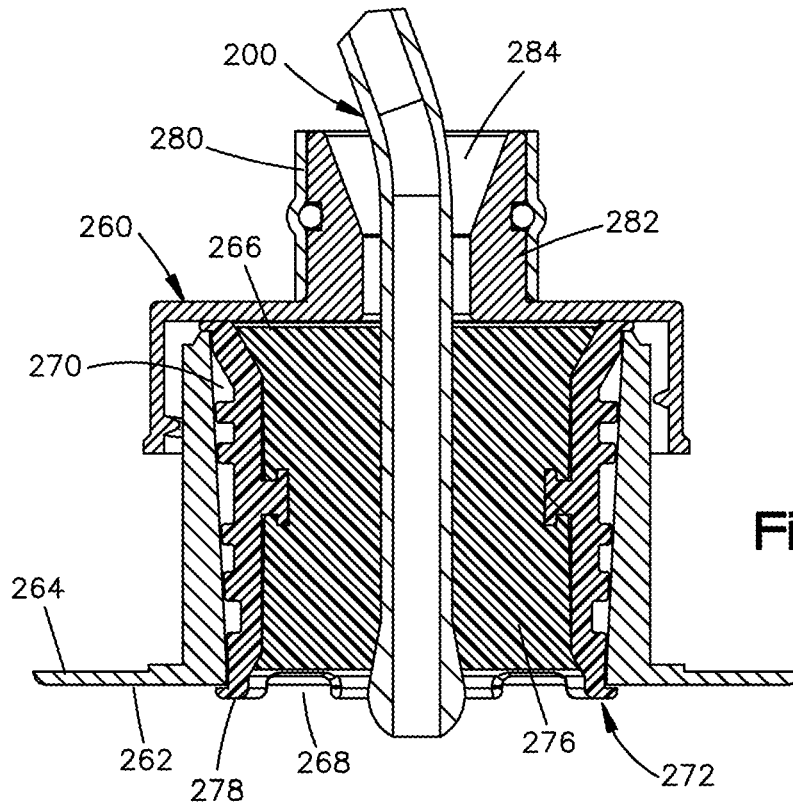
FIG. 26 is a side cross-sectional view of the port and the suction device illustrated in FIG. 25, the suction device in a third position relative to the port.

Referring to FIGS. 15 to 18, the port 160 is configured to provide access for an instrument 200, for example a suction wand 202, into the chamber interior space 102 while maintaining sterility of the chamber interior space 102. The port 160 may include a first seal 162 that is biased closed. As shown in FIGS. 15 to 17, when the instrument 200 is removed from the port 160, a slit 164 of the first seal 162 is biased closed. As shown in FIG. 18, the port 160 may include a second seal 165 that is configured to form a seal around the instrument 200 when the instrument is inserted into the port 160. According to one embodiment, the second seal 165 is spaced from the first seal 162, and the second seal 165 defines an opening 166. The opening 166 may correspond to a shape, for example match a shape, of an exterior surface of the instrument 200, such that when the instrument 200 is inserted into the port 160, the opening 166 provides a passageway for the instrument 200 and forms a seal with the instrument 200.

According to one aspect of the disclosure, the port 160 may include a third seal 168 that is moveable from a first position to a second position. As shown in FIGS. 15 and 16, in the first position, also referred to herein as a closed position, the third seal 168 blocks the passageway through the port 160, such that the instrument 200 cannot pass through the port 160 into the chamber interior space 102. As shown in FIGS. 17 and 18, the third seal 168 may be moved, for example translated, such that an opening 170 of the third seal 168 is aligned with the passageway of the port 160, and the instrument 200 can pass through the port 160 into the chamber interior space 102.

Referring to FIGS. 19 to 22, according to another embodiment, the third seal 168 of the port 160 may be similar to the second seal 164 as described above in reference to FIGS. 15 to 18, such that the third seal 168 is not movable from a first position to a second position, but rather the opening 170 is fixed in position to the passageway of the port 160 and corresponds to a shape of the instrument 200, such that when the instrument 200 is inserted into the port 160, the opening 166 provides a passageway for the instrument 200 and forms a seal with the instrument 200. As shown in the illustrated embodiment, the opening 170 may be larger than the opening 166 when instrument 200 is removed from the port 160.

Referring to FIGS. 23 to 26, the system 10 may include a port 260 instead of or in addition to the port 160. The port 260 may include a housing 262 configured to be attached to one of the first shell 114 and the second shell 116. For example, an upper surface 264 of the housing 262 may be welded to one of the flexible wall 212a and 212b, for example the side of the flexible wall 212a and 212b that faces the interior space 102. Alternatively, the housing 262 may be configured to be welded to the side of the flexible wall 212a and 212b that faces away from the interior space 102. The housing 260 defines a first opening 266, a second opening 268 and a recess 270 that extends from the first opening 266 to the second opening 268.

The port 260 further includes an insert 272 positioned within the recess 270. The insert 272 is configured to create a seal, for example a liquid-tight seal, an air-tight seal, or both, between the first opening 266 and the second opening 268. The insert 272 includes an elastically deformable material with a slit 274. The insert 272 is configured to allow the instrument 200 to be inserted into the slit 274 and form a seal around the instrument 200 as the instrument is inserted through the slit 274. The insert 272 may include a first material 276, for example silicone, configured to compress as the instrument 200 is inserted into the slit 274 and apply a biasing force against the instrument 200 thereby maintaining a seal between the first opening 266 and the second opening 268.

The insert 272 may further include a second material 278, for example a polycarbonate, that is stiffer than the first material 276. The second material 278 may be positioned around the first material 276 and may include an attachment mechanism to secure the insert 272 within the recess 270.

The port 260 may also include a cap assembly 280. The cap assembly 280 includes a body 282 that defines an opening 284 configured to guide the instrument to the slit 274. The cap assembly 280 may be attached to the housing 260, for example threadedly attached with corresponding threads.

Figure 27:
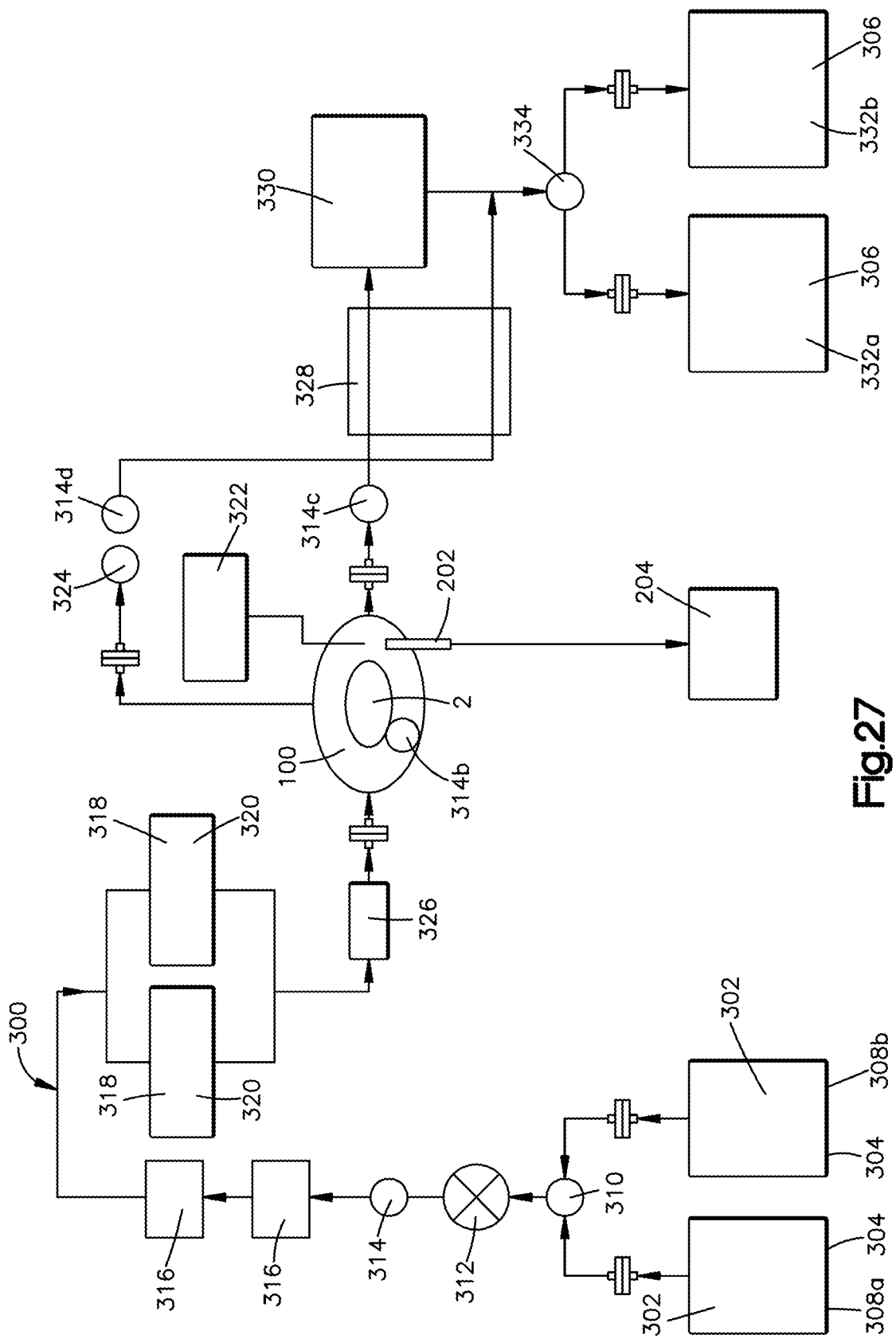
FIG. 27 is a schematic view of a first fluid circuit of the extracorporeal support system illustrated in FIG. 1.

Referring to FIG. 27, the system 10 includes a first fluid circuit 300, which is configured to deliver a fluid 302 from a source 304 to the chamber 100, and then deliver the fluid 302 from the chamber 100 to a reservoir 306. The fluid 302 may be a sterile solution, for example an electrolyte solution. The source 304 may include multiple source containers, for example a first source container 308a and a second source container 308b. The multiple source containers may be arranged in parallel such that the fluid 302 can be delivered from one or another of the multiple source containers. According to one aspect of the disclosure, the first fluid circuit 300 includes a valve 310 that is configured to provide passage of the fluid 302 from the source 304 to the chamber 100 when the valve 310 is in an open configuration, and the valve 310 is further configured to block passage of the fluid 302 from the source 304 to the chamber 100 when the valve 310 is in a closed configuration.

As shown in the illustrated embodiment, the valve 310 may be a three-way valve that includes a first open configuration in which the valve 310 provides passage of the fluid 302 from the first source container 308a to the chamber 100 while blocking passage of the fluid 302 from the second source container 308b to the chamber 100. The three-way valve may further include a second open configuration in which the valve 310 provides passage of the fluid 302 from the second source container 308b to the chamber 100 while blocking passage of the fluid 302 from the first source container 308a to the chamber 100. The valve 310 being a three-way valve as described above would allow for the fluid 302 from the first source container 308a to be delivered to the chamber 100 until the first source container 308a is empty, then the valve 310 could be transitioned from the first open configuration to the second open configuration allowing the fluid 302 from the second source container 308b to be delivered to the chamber 100, while allowing the, now empty, first source container 308a to be replaced with a new container.

The first fluid circuit 300 includes a pump 312, for example a peristaltic pump, configured to move the fluid 302 from the source 304 to the chamber 100. The first fluid circuit 300 may include a first pressure sensor 314a positioned between the pump 312 and the chamber 100, a second pressure sensor 314b positioned within the chamber 100, a third pressure sensor 314c positioned between the chamber 100 and the reservoir 306, a fourth pressure sensor 314d, or any combination thereof. Each of the pressure sensors 314a, 314b, 314c, and 314d may be configured to output a numerical value representing the current pressure within the first fluid circuit 300 between the pump 312 and the chamber 100 to a display viewable by a user of the system 10.

The first fluid circuit 300 may include a filters 316 configured to block particulates in the fluid 302 from reaching the chamber 100. The filter 316 may be configured to block particulates of a selected size, for example particles greater than about 0.22 micrometers. The filter 316 may be one of a plurality of filters 316 that can be arranged in parallel or in series. The plurality of filters 316 may be configured to block particulates of the same size, or of different sizes. For example a first of the plurality of filters 316 may be configured to block particulates of a first size, and a second of the plurality of filters 316 may be configured to block particulates of a second size. The first size may be larger than the second size, and the second of the plurality of filters 316 may be positioned between the first of the plurality of filters 316 and the chamber 100.

The first fluid circuit 300 may include a heat source 318 configured to change a temperature of the fluid 302 prior to reaching the chamber 100. The heat source 318 may include one or more heaters 320 configured to increase the temperature of the fluid 302. The first fluid circuit 300 may include a turbidity meter 322, configured to measure the clarity of the fluid 302. The turbidity meter 322 may be positioned within the chamber 100 and configured to send a signal, for example activate an alarm of the system 10, when a level of cloudiness is present within the fluid 302. Cloudiness in the fluid 302 may be caused by a contaminate in the fluid 302 in the chamber 100, for example meconium. The turbidity meter 322 may be configured to detect blood in the chamber 100. The presence of blood in the chamber 100 may signal a decannulation event, which may require rapid detection and notification to minimize potential harm to the infant 2.

The system 10 is configured to facilitate removal of the contaminate in the fluid 302 in the chamber 100 while maintaining the chamber 100 in the closed configuration. For example the suction wand 202 may be inserted into the chamber 100, for example through one of the ports as described above, and used to remove the contaminate. The suction wand 202 may be connected to a vacuum source 204, for example a mobile vacuum source or a fixed vacuum source.

The first fluid circuit 300 may include a release valve 324 configured to provide release the fluid 302 within the chamber 100 more quickly than the fluid 302 would normally exit the chamber 100 toward the reservoir 306. If the pressure of the fluid 302 within the chamber 100 reaches a value above a desired level, or if quick access to the fetus 2 is desired, actuation of the release valve 324 will empty the chamber 100 of the fluid 302 currently within the chamber 100.

The first fluid circuit 300 may include a flow meter 326 configured to measure a rate at which the fluid 302 is moving through the first fluid circuit 300. The first fluid circuit 300 may include a first flow meter 326 positioned between the pump 312 and the chamber 100 such that the first flow meter 326 is configured to measure the flow rate of the fluid 302 into the chamber 100, a second flow meter 326 positioned between the chamber 100 and the reservoir 306 such that the second flow meter 326 is configured to measure the flow rate of the fluid 302 out of the chamber 100, or both.

The first fluid circuit 300 may include a filtration system 328 positioned between the chamber 100 and the reservoir 306. The filtration system 328 is configured to prevent contaminates, such as bacteria, from migrating toward the chamber 100 along a direction that is opposite the direction of flow of the fluid 302. According to one aspect of the disclosure, the filtration system 328 is configured to kill bacterial growth that migrates from the reservoir 306 toward the chamber 100.

The first fluid circuit 300 may include a pressure regulator 330 configured to adjust the pressure of the fluid 302 within the chamber 100. The pressure regulator 330 may include an actuator that is configured to receive an input, for example a manual input that includes raising or lowering the actuator with respect to the surface the system 10 is positioned upon, to raise or lower, respectively, the pressure of the fluid 302 within the chamber 100.

Figure 28:
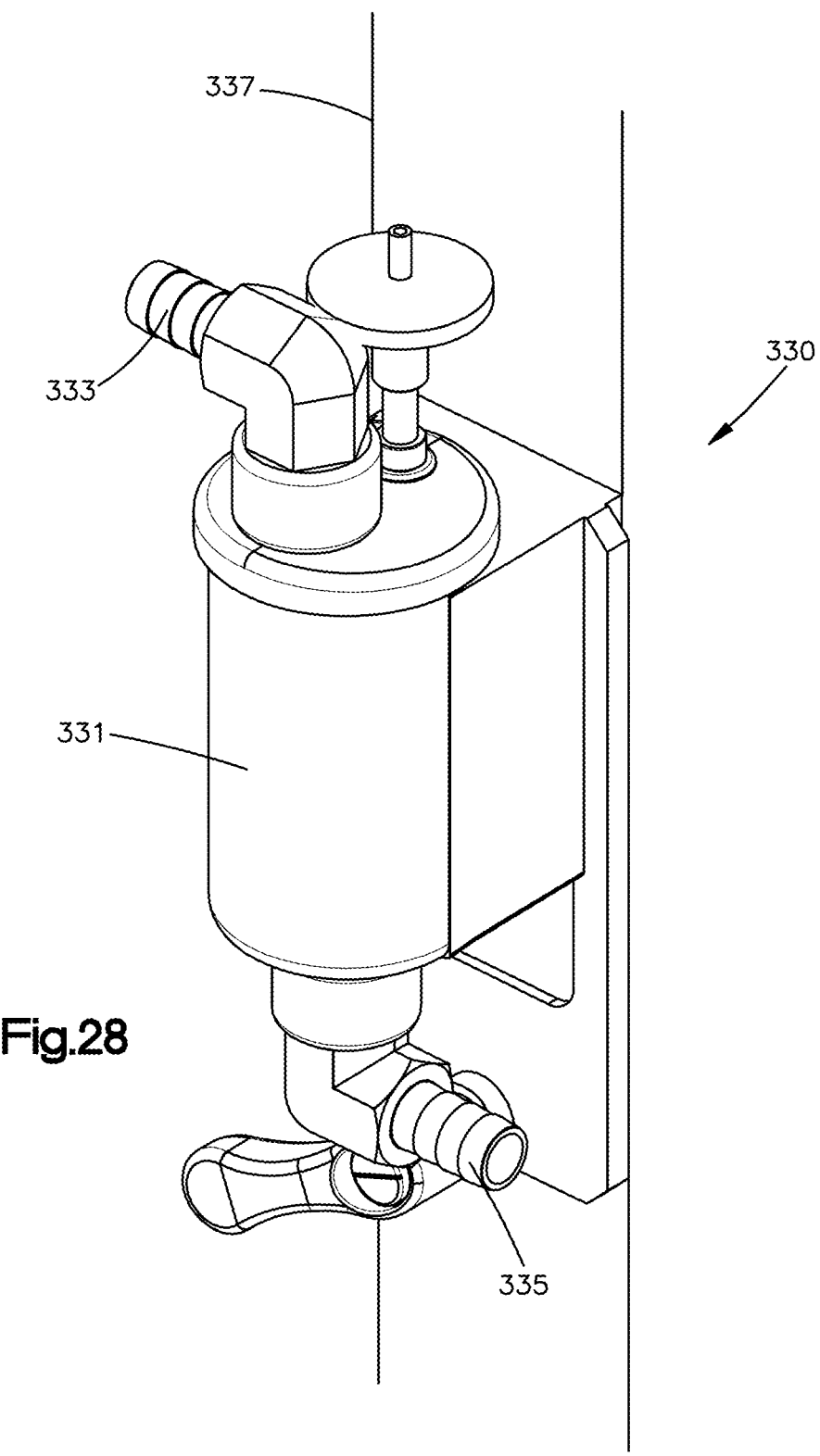
FIG. 28 is an isometric view of a pressure regulator of the first fluid circuit illustrated in FIG. 27.

Referring to FIGS. 27 and 28, the pressure regulator 330 may include a pressure chamber 331, a first port 333 coupled to the pressure chamber 331 and a second port 335 coupled to the pressure chamber 331. The pressure regulator 330 may be configured such that the fluid 302 discharged from the chamber 100 enters the pressure chamber 331 through the first port 333 and exits through the second port 335 on the way towards the reservoir 306. As shown in the illustrated embodiment, the pressure chamber 331 is slidably mounted to the cart 12, for example on a pair of rails 337. According to one aspect of the disclosure, the pressure inside the interior space 102 may be adjusted by adjusting the height of the pressure chamber 331 relative to the interior space 102. For example, the system 10 may be configured such that by sliding the pressure chamber 331 "up" along the rails 337 thereby increasing the height of the pressure chamber 331 relative to the interior space 102, the fluid 302 exiting the interior space 102 must travel "up" against gravity, thereby increasing the pressure within the interior space 102. The system 10 may further be configured such that by sliding the pressure chamber 331 "down" along the rails 337 thereby decreasing the height of the pressure chamber 331 relative to the interior space 102, the fluid 302 exiting the interior space 102 has less of a vertical distance to travel "up" against gravity, thereby decreasing the pressure within the interior space 102.

The reservoir 306 may include multiple reservoir containers, for example a first reservoir container 332a and a second reservoir container 332b. The multiple reservoir containers may be arranged in parallel such that the fluid 302 can be delivered from one or another of the multiple reservoir containers 332a and 332b. According to one aspect of the disclosure, the first fluid circuit 300 includes a valve 334 that is configured to provide passage of the fluid 302 from the chamber 100 to the reservoir 306 when the valve 334 is in an open configuration, and the valve 334 is further configured to block passage of the fluid 302 from the chamber 100 to the reservoir 306 when the valve 334 is in a closed configuration.

As shown in the illustrated embodiment, the valve 334 may be a three-way valve that includes a first open configuration in which the valve 334 provides passage of the fluid 302 from chamber 100 to the first reservoir container 332a while blocking passage of the fluid 302 from the chamber 100 to the second reservoir container 332b. The three-way valve may further include a second open configuration in which the valve 334 provides passage of the fluid 302 from the chamber 100 to the second reservoir container 332b while blocking passage of the fluid 302 from the chamber 100 to the first reservoir container 332a. The valve 334 being a three-way valve as described above would allow for the fluid 302 from the chamber 100 to be delivered to the first reservoir container 332a until the first reservoir container 332a is full, then the valve 334 could be transitioned from the first open configuration to the second open configuration allowing the fluid 302 from the chamber 100 to be delivered to the second reservoir container 332b, while allowing the, now full, first reservoir container 332a to be removed and replaced with a new, empty container.

Figure 30:
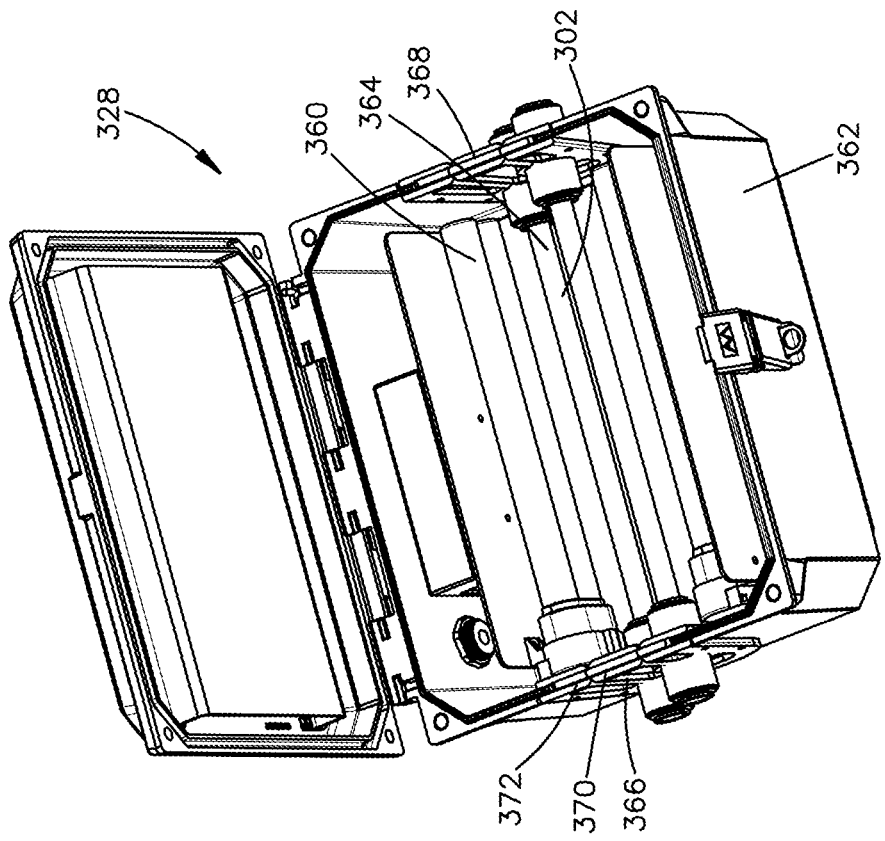
FIG. 30 is an isometric view of the sterilization unit illustrated in FIG. 29, the sterilization unit in a second configuration.
Figure 29:
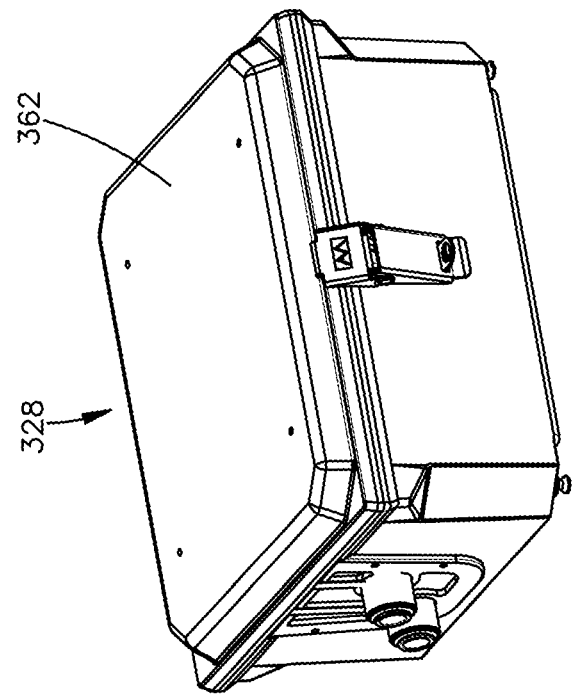
FIG. 29 is an isometric view of a sterilization unit of the extracorporeal support system illustrated in FIG. 1, the sterilization unit in a first configuration.

Referring to FIGS. 27 and 29 to 30, the filtration system 328 may include an ultraviolet light source 360 configured to deliver an amount of ultraviolet light to the fluid 302 between the chamber 100 and the reservoir 306. Bacteria or other contaminants may grow within the reservoir 306 and grow or migrate toward the chamber 100 retrograde, or opposite the flow of the fluid 302. The filtration system 328 is configured to eradicate the contaminate before the contaminate reaches the chamber 100.

The filtration system 328 may include a housing 362 configured to limit an amount of ultraviolet light that exits the filtration system 328. According to one embodiment, the housing 362 defines an open configuration (as shown in FIG. 30) and a closed configuration (as shown in FIG. 29). In the closed configuration the housing 362 is configured to block a portion, for example all, of the ultraviolet light from reaching the chamber 100. The filtration system 328 may include a length of tubing 364 that is exposed to the ultraviolet light source 360 and that carries the fluid 302 between the chamber 100 and the reservoir 306.

The housing 362 may include a first seal 366 and a second seal 368 that are each configured to receive the tubing 364 such that when the tubing 364 is positioned within the first seal 366 and the second seal 368, the first seal 366 and the second seal 368 form a light barrier around the tubing 364 preventing the ultraviolet light from exiting the housing 362. The first seal 366, the second seal 368, or both may include a slot 370 extending from an outer surface 372 in a direction substantially perpendicular to the direction of flow of the fluid 302 within the tubing 364. The slot 370 may be configured to facilitate sliding engagement of the tubing 364 with the respective seal. The housing 362 may include a reflective surface 374 positioned within the housing 362 such that the reflective surface 374 is configured to reflect the ultraviolet light to additional areas of the tubing 364 that are not directly exposed to the ultraviolet light source 360.

The filtration system 328 defines a length L3 measured along the section of tubing that is exposed to the ultraviolet light and measured in the direction of the flow of the fluid 302. According to one aspect of the disclosure, the length L3 is greater than about 0.8 inches, the irradiance provided by the ultraviolet light source 360 is about 100 microwatts per centimeter squared, the cross-sectional area of the tubing 364 is about 0.22 centimeters squared, and the flowrate of the fluid 302 through the tubing 364 may be up to about 32 milliliters per minute.

Thus a method of providing care for the fetus 2, for example the method of moving the fetus 2 from the uterus of a patient 6 to an ex utero environment, may include the step of exposing a portion of a first fluid circuit 300 that flows through the chamber 100 to ultraviolet light.

Figure 31:
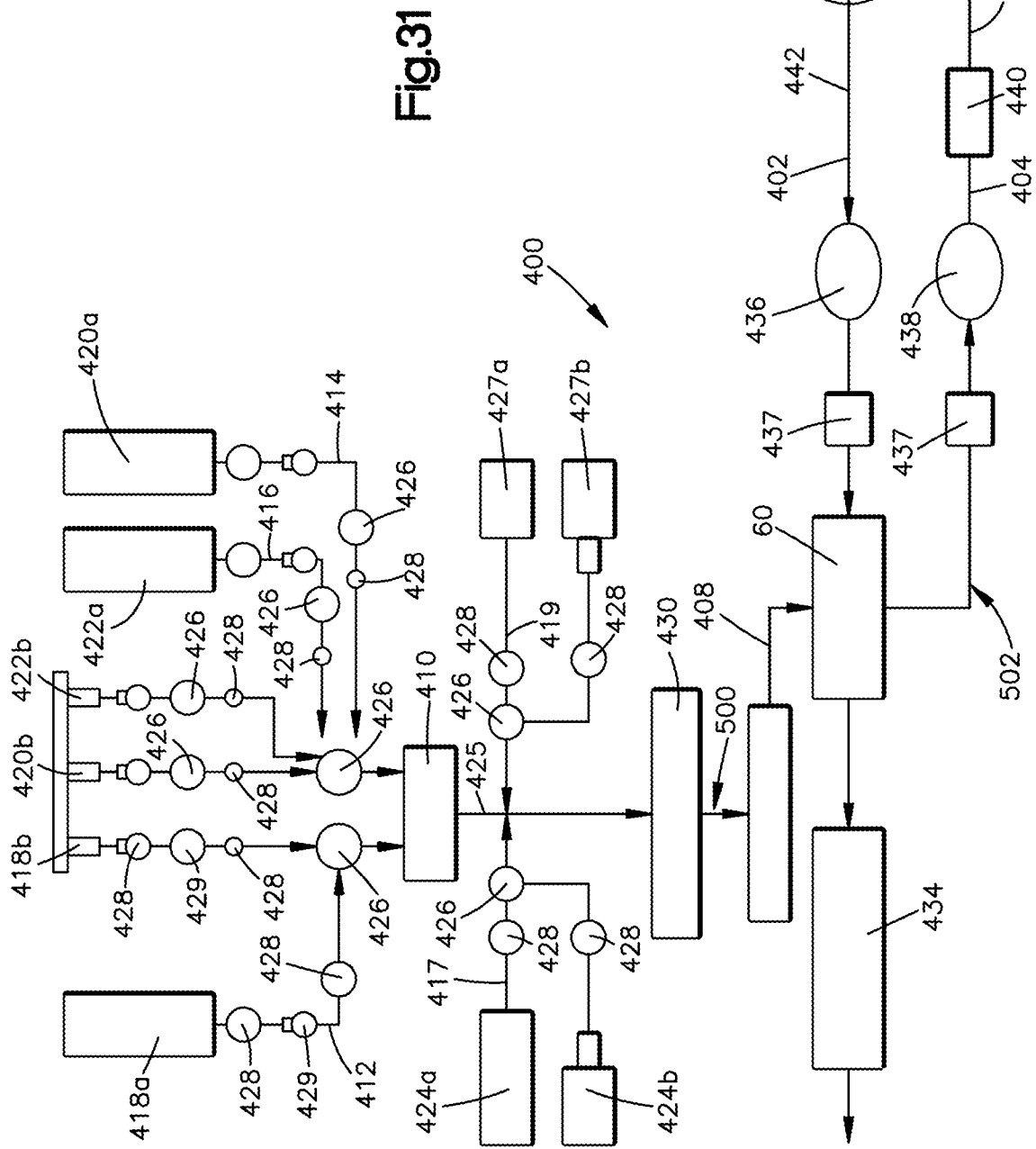
FIG. 31 is a schematic view of a second fluid circuit of the extracorporeal support system illustrated in FIG. 1.

Referring to FIG. 31, the system 10 includes a second fluid circuit 400 configured to provide gas transfer between the fetus 2 and the oxygenator 60. Specifically, the second fluid circuit 400 is configured to provide oxygen to and remove carbon dioxide from the blood of the fetus 2. The second fluid circuit 400 may include a first portion 500 configured to deliver a sweep gas 408 to the oxygenator 60, and a second portion 502 configured to accept the sweep gas 408 and perform gas exchange with the blood supply of the fetus 2. The second portion 502 may include the oxygenator 60 connected with the fetus 2 by two fluid lines of the second fluid circuit 400. The two fluid lines include an outflow line 402 and an inflow line 404. The blood of the fetus 2 flows from the fetus 2 though the outflow line 402 to the oxygenator 60, the blood then flows through the oxygenator 60 and returns to the fetus 2 through the inflow line 404. The outflow line 402 and the inflow line 404 pass through the seal 120, for example by way of the cannulae 140.

The system 10 may be configured such that the oxygenator 60 is positioned close to the chamber 100 such that the lengths of the outflow line 402 and the inflow line 404, to and from the oxygenator 60 respectively, are minimized. For instance, in accordance with one aspect of the disclosure, the outflow line 402 and the inflow line 404 are less than about 36 inches long combined. By minimizing the lengths of the outflow line 402 and the inflow line 404, the volume of blood required to prime the second fluid circuit 400 is minimized. It may be desirable to line the outflow line 402 the inflow line 404, or both with anti-clotting measures/compounds (for example, but not limited to, immobilized polypeptide, heparin, or both).

The oxygenator 60 may be primed prior to connection with the fetus 2. According to one embodiment, the oxygenator 60 may be primed with a crystalloid solution containing human albumin. The second fluid circuit 400 may then be further primed with, for example, maternal blood, blood of the fetus 2, or both. Priming of the second fluid circuit 400 with hemoglobin from the fetus 2 may result in optimal oxygen exchange in the second fluid circuit 400. Because the fetal oxygen dissociation curve is shifted to the left compared to the adult oxygen dissociation curve, fetal arterial oxygen pressures are lower than adult arterial oxygen pressures. In a one embodiment, the blood in the second fluid circuit 400 includes heparin. According to another embodiment, the blood in the second fluid circuit 400 is devoid of heparin.

According to one aspect of the disclosure, the first portion 500 of the second fluid circuit 400 produces a sweep gas 408 and delivers the sweep gas 408 to the oxygenator 60, the sweep gas 408 is configured to facilitate gas transfer between the oxygenator 60 and the blood of the fetus 2. The gas transfer is affected by the composition of the sweep gas 408 and the flow rate of the sweep gas 408 through the oxygenator 60. A plurality of gases may be blended together in a gas blender 410 that blends the plurality of gases to form the sweep gas. According to one aspect of the disclosure, the plurality of gases may include, but is not limited to, oxygen, nitrogen, carbon dioxide, nitric oxide, air, or any combination thereof. As shown in the illustrated embodiment, the plurality of gases may include at least a first gas 412 and a second gas 414. The plurality of gases may further include a third gas 416, a fourth gas 417, a fifth gas 419, or any combination thereof. According to one aspect of the disclosure, any or all of the plurality of gases may be supplied by multiple sources such as a mobile, smaller source, and a larger, fixed source.

As an example, the second fluid circuit 400 may include a mobile first gas source 418a, for example that is attached to and carried by the cart 12, and a fixed first gas source 418b that is fixed in place, for example as part of the infrastructure of a hospital room. The second fluid circuit 400 may further include a mobile second gas source 420a, a fixed second gas source 420b, a mobile third gas source 422a, a fixed third gas source 422b, a mobile fourth gas source 424a, a fixed fourth gas source 424b, a mobile fifth gas source 427a, a fixed fifth gas source 427b, or any combination thereof.

The first portion 500 of the second fluid circuit 400 may include a plurality of valves 426 each configured to control whether the mobile or fixed source of each respective gas source is connected with the second fluid circuit 400. The second fluid circuit 400 may include one or more pressure sensors 428 positioned inline with each of the plurality of gas supplies, the plurality of pressure sensors 428 configured to measure the gas pressure of the plurality of gases being fed to the second fluid circuit 400. The second fluid circuit 400 may further include one or more pressure regulators 429 configured to provide receive a variable pressure from the respective gas source and deliver a steady, constant pressure of the respective gas. As shown in the illustrated embodiment, the pressure regulator 429 may be positioned between two of the pressure sensors 428, which may be configured to measure the pressure going into and coming out of the pressure regulator 429.

The second fluid circuit 400 may be configured such that one or more of the plurality of gases enter the gas blender 410. As shown in the illustrated embodiment, the first gas 412 and one of the second gas 414 and the third gas 416 may enter the gas blender 410. According to one aspect of the disclosure, the first gas 412 is oxygen, the second gas 414 is nitrogen, and the third gas 416 is air. The gas blender 410 outputs a mixed gas 425. The second fluid circuit 400 may be configured such that one or more of the plurality of gases combines with the mixed gas 425 after the mixed gas 425 exits the gas blender 410. According to one embodiment, the plurality of gases includes oxygen, nitrogen, and air coupled to the second fluid circuit 400 such that the oxygen and one of nitrogen and the air enter the gas blender 410 to form the mixed gas 425. The second fluid circuit 400 may include the fourth gas 417, the fifth gas 419, or both connected to the mixed gas 425 to form the sweep gas 408. The fourth gas may include carbon dioxide and the fifth gas may include nitric oxide, according to one aspect of the disclosure that are each configured to be added to the mixed gas 425 after the mixed gas 425 exits the gas blender 410, to form the sweep gas 408.

The second fluid circuit 400 may include a heater, for example the heater 42, or a different heater that is positioned inline between the gas blender 410 and the oxygenator 60, the heater configured to heat the sweep gas 408 so that the temperature of the sweep gas 408 is maintained within a predetermined range. The second fluid circuit 400 may include a fluid flow regulator 430 configured to monitor, adjust, or both the flow rate of the sweep gas 408. The second fluid circuit 400 may further include a sweep gas analyzer 432 configured to analyze one or more characteristics of the sweep gas 408 entering the oxygenator 60.

The second fluid circuit 400 may include an exhaust gas analyzer 434 configured to analyze one or more characteristics of the gas discharged by the oxygenator 60. For instance, the gas analyzers 432 and 434 may be configured to measure the oxygen content of the sweep gas and the exhaust gas, respectively. As shown in the illustrated embodiment, the fluid flow regulator 430 may be positioned between the sweep gas analyzer 432 and the oxygenator 60.

The second fluid circuit 400 further includes a pair of fluid pressure sensors 436 and 438 configured to detect the fluid pressure of the blood entering the oxygenator 60 and the fluid pressure of the blood exiting the oxygenator 60, respectively. Specifically, the first pressure sensor 436 may be positioned in-line with the outflow line 402 and the second pressure sensor 438 may be positioned in-line with the inflow line 404. In this way, the fluid pressure drop over the oxygenator 60 can be continuously monitored. Additionally, a fluid flow meter 440 may be positioned in-line with the inflow line 404 to monitor the flow rate of the blood returning to the fetus 2 from the oxygenator 60.

The second fluid circuit 400 may include one or more ports 442, which may be utilized to withdraw blood samples for analysis or the ports 442 may be used to inject or infuse medicine or nutrition directly into the blood. For instance, one of the ports 442 may be configured to facilitate injection of medication such as antibiotics or sedatives into the blood. Similarly, another of the ports 442 may be configured to facilitate injection of nutrition such as total parental nutrition (TPN) into the blood.

The second portion 502 of the second fluid circuit 400 may include a first sensor 437 and a second sensor 439 positioned such that the oxygenator 60 is between, for example directly between, the first sensor 437 and the second sensor 439. The first sensor 437 and the second sensor 439 may configured to measure one or more variables of the blood of the fetus 2 just before entering the oxygenator 60 and just after exiting the oxygenator 60, respectively, so that the change provided by the oxygenator can be measured and monitored. The first sensor 437 and the second sensor 439 may each be configured to measure blood flow, blood oxygen levels, blood hemoglobin levels, or any combination thereof. According to one embodiment, the first sensor 437 and the second sensor 439 each use absorbance spectroscopy to measure the amount of oxygen bound to hemoglobin, and levels of hemoglobin. Blood flow may be measured by ultrasound.

In accordance with one aspect of the disclosure, the heart of the fetus 2 drives blood flow through the second portion 502 of the second fluid circuit 400, such that the second portion 502 of the second fluid circuit 400 is devoid of a pump. In other words, according to one aspect of the disclosure, the second portion 502 of the second fluid circuit 400 is a pumpless circuit. The use of a pumpless system avoids exposure of the heart of the fetus 2 to excess preload encountered in non-pulsatile pump-assisted circuits. The pumpless system also permits intrinsic fetal circulatory regulation of flow dynamics. The oxygenator 60 preferably has very low resistance, low priming volume, low transmembrane pressure drops, and provides efficient gas exchange. The first portion 500 of the second fluid circuit 400 may be driven by an external pressure source.

In accordance with one embodiment, the oxygenator 60 has a pressure drop of less than about 50 mmHg or about 40 mmHg at 1.5 liters per minute of blood flow. In a particular embodiment, the priming volume of the oxygenator 60 is less than about 100 milliliters and in particular is less than about 85 milliliters. In a particular embodiment, the oxygenator 60 has a blood flow range up to about 2.0 liters per minute, about 2.5 liters per minute, about 2.8 liters per minute, or greater. In a particular embodiment, the oxygenator 60 has a gas transfer rate of about 150 milliliters per minute, about 160 milliliters per minute, about 180 milliliters per minute, or greater for oxygen. In a particular embodiment, the oxygenator 60 is a hollow fiber membrane oxygenator (for example, but not limited to, a polymethyl pentene hollow fiber membrane oxygenator). The oxygenator 60 may be lined with anti-clotting measures/compounds such as immobilized polypeptide and/or heparin).

The system 10 may be configured for use with fetuses, including term and preterm fetuses. The preterm fetus may be a premature fetus (for example, less than 37 weeks estimated gestational age, particularly 28 to 32 weeks estimated gestational age), extreme premature fetuses (24 to 28 weeks estimated gestational age), or pre-viable fetuses (20 to 24 weeks estimated gestational age). The gestation periods are provided for humans, though corresponding preterm fetuses of other animals may be used. In a particular embodiment, the preterm fetus has no underlying congenital disease. In a particular embodiment, the term or preterm fetus has limited capacity for pulmonary gas exchange, for example, due to pulmonary hypoplasia or a congenital anomaly affecting lung development, such as congenital diaphragmatic hernia. In a particular embodiment, the subject is a preterm or term neonate awaiting lung transplantation, for example, due to congenital pulmonary disease (e.g., bronchoalveolar dysplasia, surfactant protein B deficiency, and the like). Such transplantation surgeries are currently rarely performed in the United States. However, the number of transplantation surgeries may be increased with the more stable method for pulmonary support provided by the instant invention. The fetus 2 may also be a candidate for ex utero intrapartum treatment (EXIT) delivery, including patients with severe airway lesions and a long expected course before definitive resection. The fetus 2 may also be a fetal surgical or fetoscopic procedure patient, particularly with preterm labor precipitating early delivery. According to one aspect of the disclosure the system 10 is configured such that the fetus 2 may be maintained in the system 10 for as long as needed (for example, for days, weeks or months, until the fetus 2 is capable of life without the system 10).

It will be appreciated that the foregoing description provides examples of the disclosed system and methods. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

Recitation of ranges of values herein are merely intended to serve as a shorthand method of referring individually to each separate value falling within the range including the stated ends of the range, unless otherwise indicated herein, and each separate value is incorporated into the specification as if it were individually recited herein. All methods described herein can be performed in any suitable order unless otherwise indicated herein or otherwise clearly contradicted by context.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A chamber configured to enclose a neonate within an interior space of the chamber, the chamber comprising:
    an outer wall that defines an outer boundary of the interior space;
    an inner wall that extends from the outer wall into the interior space such that the inner wall partially defines both a first portion of the interior space and a second portion of the interior space and separates the first portion from the second portion;
    a clamp positioned within the second portion, the clamp movable in a direction from one of the outer wall and the inner wall toward the other of the outer wall and the inner wall; and
    an actuator operably coupled to the clamp such that movement of the actuator moves the clamp in the direction.

2. The chamber of claim 1, wherein the chamber includes a first shell having the outer wall, the inner wall, and the clamp, and the chamber further includes a second shell that cooperates with the first shell to at least partially define the interior space, the chamber configured such that the second shell is movable with respect to the first shell from a first position to a second position, such that in the first position the chamber is in an open configuration, and in the second position the chamber is in a closed configuration.

3. The chamber of claim 2, wherein when the chamber is in the open configuration the first shell and the second shell cooperatively define an opening into the interior space, the opening defines a first distance measured from a portion of the first shell to a portion of the second shell, and when the chamber is in the closed configuration the opening defines a second distance measured from the portion of the first shell to the portion of the second shell, and the second distance is less than the first distance.

4. The chamber of claim 1, wherein the first portion of the interior space is adapted to receive the neonate.

5. The chamber of claim 1, wherein the inner wall includes a first end and a second end spaced from the first end along a central axis, the first end coupled to the outer wall, and
    wherein the inner wall includes a first side and a second side spaced from the first side along a lateral axis perpendicular to the central axis, the first side facing the first portion and the second side facing the second portion.

6. A chamber configured to enclose a neonate within an interior space of the chamber, the chamber comprising:
    an outer wall that defines an outer boundary of the interior space;
    an inner wall that extends from the outer wall into the interior space such that the inner wall partially defines both a first portion of the interior space and a second portion of the interior space;
    a clamp positioned within the second portion, the clamp movable in a direction from one of the outer wall and the inner wall toward the other of the outer wall and the inner wall; and
    an actuator operably coupled to the clamp such that movement of the actuator moves the clamp in the direction,
    wherein the first portion defines a first maximum dimension measured from a first point on the outer wall to a second point on the outer wall, the second portion defines a second maximum dimension measured from the first point on the outer wall to a first point on the inner wall, and the first maximum dimension is greater than the second maximum dimension.

7. The chamber of claim 6, wherein the direction is a first direction, the chamber further comprising a seal positioned within a recess at least partially defined by the outer wall, the seal including a first surface that faces toward the outer wall, a second surface that is opposite the first surface with respect to a second direction that is perpendicular to the first direction such that the second surface faces away from the outer wall, and a slot that extends from the second surface of the seal toward the first surface of the seal along the second direction such that the slot terminates prior to reaching the first surface.

8. The chamber of claim 7, wherein the slot faces the second portion along a third direction that is perpendicular to the second direction.

9. A system configured to provide oxygen to a neonate, the system comprising:
    a cart including a housing that defines a housing interior space;
    a chamber configured to enclose the neonate within an interior space of the chamber, the chamber comprising:
        an outer wall that defines an outer boundary of the interior space;
        an inner wall that extends from the outer wall into the interior space such that the inner wall partially defines both a first portion of the interior space and a second portion of the interior space;
        a clamp positioned within the second portion, the clamp movable in a direction from one of the outer wall and the inner wall toward the other of the outer wall and the inner wall; and
        an actuator operably coupled to the clamp such that movement of the actuator moves the clamp in the direction;
    a first fluid circuit including a source of a liquid, a pump configured to move the liquid from the source to the chamber, the pump further configured to move the liquid from the chamber to a reservoir; and
    a second fluid circuit including an oxygenator configured to transfer oxygen to the neonate;
    wherein the system defines a first configuration in which both the chamber and the oxygenator are positioned outside of the housing interior space, and the chamber is disconnected from the first fluid circuit and
    wherein the system defines a second configuration in which both the chamber and the oxygenator are positioned within the housing interior space, and the chamber is in fluid connection with the first fluid circuit.

10. The system of claim 9, wherein the housing includes a plurality of side walls, a base surface, and a lid that cooperate to define the housing interior space.

11. The system of claim 9, wherein the chamber is rotatable about an axis relative to the cart.

12. The system of claim 9, further comprising a filtration system positioned between the chamber and the reservoir, the filtration system configured to prevent contaminates from migrating toward the chamber.

13. The system of claim 12, wherein the filtration system includes an ultraviolet light source enclosed within a housing that is configured to prevent at least some of the ultraviolet light from reaching the chamber.

14. The system of claim 9, wherein the second fluid circuit includes a first portion configured to deliver a sweep gas to the oxygenator, and the second fluid circuit includes a second portion configured to accept the sweep gas and perform gas exchange with the neonate.

15. The system of claim 14, wherein the first portion of the second fluid circuit includes a first gas source and a second gas source that each are connected to a gas blender.

16. The system of claim 15, wherein at least one of the first gas source and the second gas source includes a mobile source enclosed within the housing interior space and a fixed source positioned at least partially outside the housing interior space.

17. The system of claim 9, further comprising a camera configured to detect blood within the interior space of the chamber.

\* \* \* \* \*